United States Patent
Ebert et al.

(10) Patent No.: US 10,272,061 B2
(45) Date of Patent: *Apr. 30, 2019

(54) COMPOSITIONS AND METHODS FOR UNOCCLUDED TRANSDERMAL OXYBUTYNIN THERAPY

(71) Applicant: Allergan Sales, LLC, Irvine, CA (US)

(72) Inventors: Charles D. Ebert, Salt Lake City, UT (US); Steven W. Sanders, Salt Lake City, UT (US)

(73) Assignee: ALLERGAN SALES, LLC, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/348,478

(22) Filed: Nov. 10, 2016

(65) Prior Publication Data

US 2017/0095438 A1 Apr. 6, 2017

Related U.S. Application Data

(60) Continuation of application No. 12/236,585, filed on Sep. 24, 2008, now abandoned, which is a division of
(Continued)

(51) Int. Cl.
*A61K 9/00* (2006.01)
*A61K 9/06* (2006.01)
*A61K 9/16* (2006.01)
*A61K 9/70* (2006.01)
*A61F 13/00* (2006.01)
*A61K 47/10* (2017.01)
(Continued)

(52) U.S. Cl.
CPC .......... *A61K 31/216* (2013.01); *A61K 9/0014* (2013.01); *A61K 9/0019* (2013.01); *A61K 9/06* (2013.01); *A61K 9/1647* (2013.01); *A61K 9/7061* (2013.01); *A61K 47/10* (2013.01); *A61F 2013/00646* (2013.01); *A61K 9/0024* (2013.01); *A61K 47/14* (2013.01); *A61K 47/38* (2013.01)

(58) Field of Classification Search
None
See application file for complete search history.

(56) References Cited

U.S. PATENT DOCUMENTS 4,590,190 A * 5/1986 Saito .................... A61K 9/0014
514/221
4,654,209 A * 3/1987 Leslie .................... A61K 9/107
424/78.25

* cited by examiner

*Primary Examiner* — Isis A Ghali
(74) *Attorney, Agent, or Firm* — Florek & Endres PLLC; Martin P Endres

(57) ABSTRACT

The present invention provides compositions and methods for administering oxybutynin while minimizing the incidence and/or severity of adverse drug experiences associated with oxybutynin therapy. In one aspect, these compositions and methods provide a lower plasma concentration of oxybutynin metabolites, such as N-desethyloxybutynin, which is presumed to be contributing at least in part to some of the adverse drug experiences, while maintaining sufficient oxybutynin plasma concentration to benefit a subject with oxybutynin therapy. The invention also provides isomers of oxybutynin and its metabolites that meet these characteristics of minimized incidence and/or severity of adverse drug experiences, and maintenance of beneficial and effective therapy for overactive bladder. In some aspects, the composition may be presented in the form of an unoccluded or free form topically administered gel.

8 Claims, 7 Drawing Sheets

Related U.S. Application Data application No. 11/645,076, filed on Dec. 21, 2006, now Pat. No. 8,241,662, which is a continuation of application No. 10/913,019, filed on Aug. 6, 2004, now Pat. No. 7,179,483, which is a continuation-in-part of application No. 10/286,381, filed on Nov. 1, 2002, now Pat. No. 7,029,694, which is a continuation-in-part of application No. 10/098,752, filed on Mar. 15, 2002, now Pat. No. 6,743,441, which is a continuation of application No. 09/559,711, filed on Apr. 26, 2000, now abandoned.

(51) Int. Cl.
*A61K 47/14* (2017.01)
*A61K 47/38* (2006.01)
*A61K 31/216* (2006.01)

COMPOSITIONS AND METHODS FOR UNOCCLUDED TRANSDERMAL OXYBUTYNIN THERAPY

PRIORITY

This application is a continuation of U.S. patent application Ser. No. 12/236,585, filed Sep. 24, 2008, which is a divisional application of U.S. patent application Ser. No. 11/645,076, filed Dec. 21, 2006, now issued as U.S. Pat. No. 8,241,662, which in turn is a continuation of U.S. patent application Ser. No. 10/913,019, filed Aug. 6, 2004, now issued as U.S. Pat. No. 7,179,483, which is a continuation-in-part of U.S. patent application Ser. No. 10/286,381, filed Nov. 11, 2002, now issued as U.S. Pat. No. 7,029,694, which is a continuation-in-part of U.S. patent application Ser. No. 10/098,752, filed Mar. 15, 2002, now issued as U.S. Pat. No. 6,743,441, which is a continuation of U.S. patent application Ser. No. 09/559,711, filed Apr. 26, 2000, now abandoned, each of which are incorporated herein by reference.

FIELD OF THE INVENTION

The present invention relates to compositions and methods for minimizing adverse drug experiences associated with oxybutynin therapy. Accordingly, this invention covers the fields of pharmaceutical sciences, medicine and other health sciences.

BACKGROUND OF THE INVENTION

Oral oxybutynin therapy is currently used for treating various forms of overactive bladder and urinary incontinence. Particularly, oxybutynin effectively treats neurogenically caused bladder disorders. Relief from such disorders is attributed to the anticholinergic and antispasmodic action which oxybutynin imparts to the parasympathetic nervous system and the urinary bladder detrusor muscle.

It is generally believed that, while this anticholinergic activity contributes to oxybutynin's clinical usefulness, it also contributes to certain uncomfortable adverse drug experiences such as dry mouth, dizziness, blurred vision, and constipation. More specifically, these experiences have been generally attributed to the presence and amount of active metabolites of oxybutynin, for example, N-desethyloxybutynin. The above-referenced adverse drug experiences are observed in a majority of patients using current oxybutynin formulations. In some cases, these adverse experiences are severe enough to persuade the patient to discontinue treatment.

In view of the foregoing, compositions and methods for administering oxybutynin to help minimize the incidence and/or severity of the above-described adverse drug experiences are extremely desirable.

SUMMARY OF THE INVENTION

Accordingly, the present invention provides methods of minimizing an adverse drug experience associated with oxybutynin therapy which comprises the step of administering a pharmaceutical composition comprising oxybutynin to a subject such that the ratio of area under the plasma concentration-time curve (AUC) of oxybutynin to an oxybutynin metabolite is about 0.5:1 to about 5:1. The adverse drug experience may be any adverse experience resulting from administration of oxybutynin, for example, anticholinergic, and/or antimuscarinic in nature.

Specific examples of known oxybutynin adverse experiences include but are not limited to: gastrointestinal/genitourinary experiences, nervous system experiences, cardiovascular experiences, dermatological experiences, and ophthalmic experiences, among others.

Oxybutynin has a chiral molecular center, leading to the presence of (R)- and (S)-isomers. When metabolized, oxybutynin gives rise to metabolites such as N-desethyloxybutynin, which may also be present as (R)- and (S)-isomers or a combination thereof. The method of the present invention specifically encompasses each isomer for both oxybutynin and its any corresponding metabolites. For example, in one aspect, the mean plasma AUC ratio of (R)-oxybutynin to (S)-oxybutynin is about 0.7:1. In another aspect, the mean AUC ratio of (R)—N-desethyloxybutynin to (R)-oxybutynin is from about 0.4:1 to about 1.6:1. In one aspect, this mean AUC ratio may be about 1:1. In another aspect, the mean AUC ratio of (R)—N-desethyloxybutynin to (S)—N-desethyloxybutynin is from about 0.5:1 to about 1.3:1. For example, this mean AUC ratio may be about 0.9:1. In another aspect, the metabolite may have a mean peak plasma concentration of less than about 8 ng/ml.

A pharmaceutical composition for administering oxybutynin to a subject is also provided, comprising oxybutynin that provides an AUC ratio of oxybutynin to an oxybutynin metabolite of from about 0.5:1 to about 5:1.

Delivery formulations useful in conjunction with the method of the present invention include but are not limited to: oral, parenteral, transdermal, inhalant, or implantable formulations. In one aspect of the invention, the delivery formulation may be a transdermal delivery formulation. In a more specific aspect, the delivery formulation may be a gel formulation that is topically administered to the skin in an unoccluded, or free form manner.

The composition of the present invention may include a pharmaceutically acceptable carrier, and other ingredients as dictated by the particular needs of the specific dosage formulation. Such ingredients are well known to those skilled in the art. See for example, Gennaro, A. *Remington: The Science and Practice of Pharmacy* 19$^{th}$ ed. (1995), which is incorporated by reference in its entirety. For example, a transdermal formulation may include, but is not limited to, permeation enhancers, anti-irritants, adhesion adjusters, and combinations thereof.

In one aspect, the formulation of the present invention may be an oxybutynin gel formulation for topical application. Such a gel may include a therapeutically effective amount of oxybutynin and a gel carrier, wherein the formulation has a pH of from about 4 to about 11 and wherein the oxybutynin is present as an oxybutynin free base, a pharmaceutically acceptable oxybutynin salt, or a mixture thereof, and wherein the formulation is prepared for unoccluded topical application to a skin surface. In another aspect, the pH of the formulation may be from about 4 to about 11. In a further aspect, the pH of the formulation may be from about 5 to about 11. In yet a further aspect, the pH of the formulation may be from about 6 to about 11. In an additional aspect, the pH of the formulation may be from about 4 to about 10. In another aspect, the pH of the formulation can be from about 5 to about 10. In an additional aspect, the pH of the formulation can be from about 6 to about 10. In a more detailed aspect, the pH of the formulation may be about 6. In yet another detailed aspect of the invention, the pH of the formulation is about 9.

According to another aspect of the invention, a gel formulation for topical application is presented which includes a therapeutically effective amount of oxybutynin in a gel carrier, which upon unoccluded topical administration, is sufficient to provide an oxybutynin skin permeation rate of at least about 10 ug/cm² over a period of at least about 24 hours.

In a further aspect of the invention, a gel formulation for topical application is presented which includes a therapeutically effective amount of oxybutynin in a gel carrier, which upon unoccluded topical administration, is sufficient to achieve an oxybutynin plasma concentration of at least about 0.5 ng/ml within at least about 3 hours after initiation of administration.

In another aspect of the invention, a gel formulation is provided for topical application that includes a therapeutically effective amount of oxybutynin in a gel carrier, which upon unoccluded topical administration, is sufficient to achieve an oxybutynin plasma concentration that is from about 0.5 to about 5 times an oxybutynin metabolite plasma concentration.

In an additional aspect of the invention, a gel formulation for topical application is provided that includes a therapeutically effective amount of oxybutynin in a gel carrier, which upon unoccluded topical administration, is sufficient to achieve a therapeutically effective oxybutynin concentration and a maximum oxybutynin metabolite plasma concentration of less than about 8 ng/ml.

In addition to the compositions recited herein, the present invention additionally encompasses a method for treating neurogenic bladder disorders in a subject which includes topically applying a gel formulation as recited herein to a skin surface of the subject. Moreover, the present invention includes a method of minimizing adverse side effects associated with oxybutynin therapy includes applying an oxybutynin gel formulation as recited herein to a skin surface a subject.

In another aspect of the present invention, an oxybutynin gel formulation for topical administration is provided, having a therapeutically effective amount of oxybutynin in a gel carrier, which upon unoccluded topical administration, is sufficient to provide a plasma AUC ratio of oxybutynin serum level to an oxybutynin metabolite serum level from about 0.75:1 to about 3:1. In another aspect, the ratio may be from about 0.98:1 to about 2:1. In a further aspect, the oxybutynin serum concentration may be greater than an oxybutynin metabolite serum concentration.

In yet another aspect of the present invention, a method of treating with oxybutynin a subject having overactive bladder is provided. The method may include the step of topically administering to a subject an oxybutynin gel formulation, which upon unoccluded topical administration, is sufficient to provide a plasma AUC ratio of oxybutynin serum level to an oxybutynin metabolite serum level from about 0.75:1 to about 3:1, in order to minimize an anticholinergic or antimuscarinic adverse drug experience associated with oxybutynin treatment therapy.

There has thus been outlined, rather broadly, the more important features of the invention so that the detailed description thereof that follows may be better understood, and so that the present contribution to the art may be better appreciated. Other features of the present invention will become clearer from the following detailed description of the invention, taken with the accompanying drawings and claims, or may be learned by the practice of the invention.

DETAILED DESCRIPTION

A. Definitions

Figure 1:
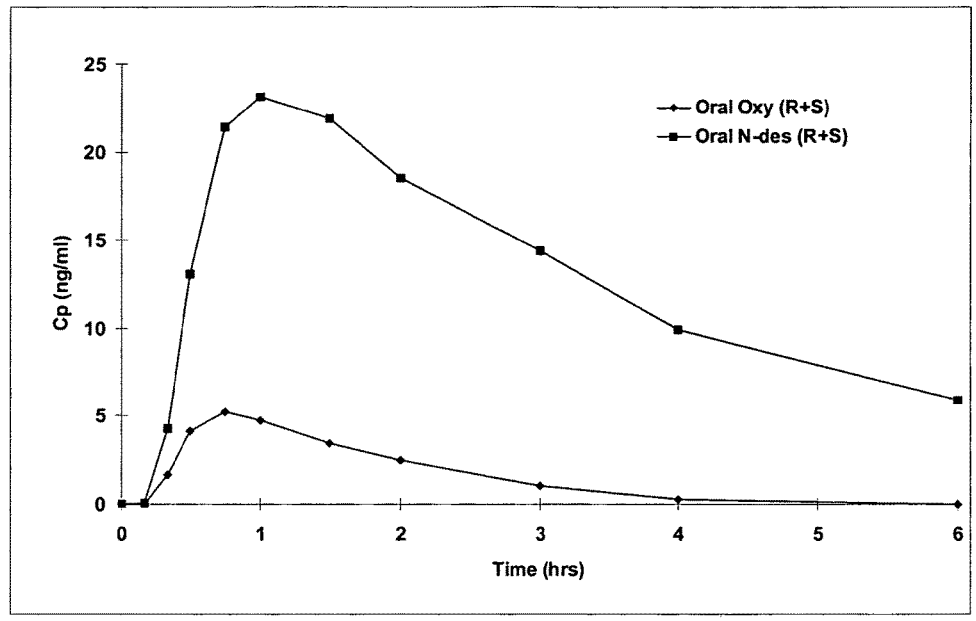
FIG. 1 is a graphical representation of total oxybutynin and N-desethyloxybutynin plasma concentrations measured following a 5 mg oxybutynin immediate-release oral dosage formulation.
Figure 2:
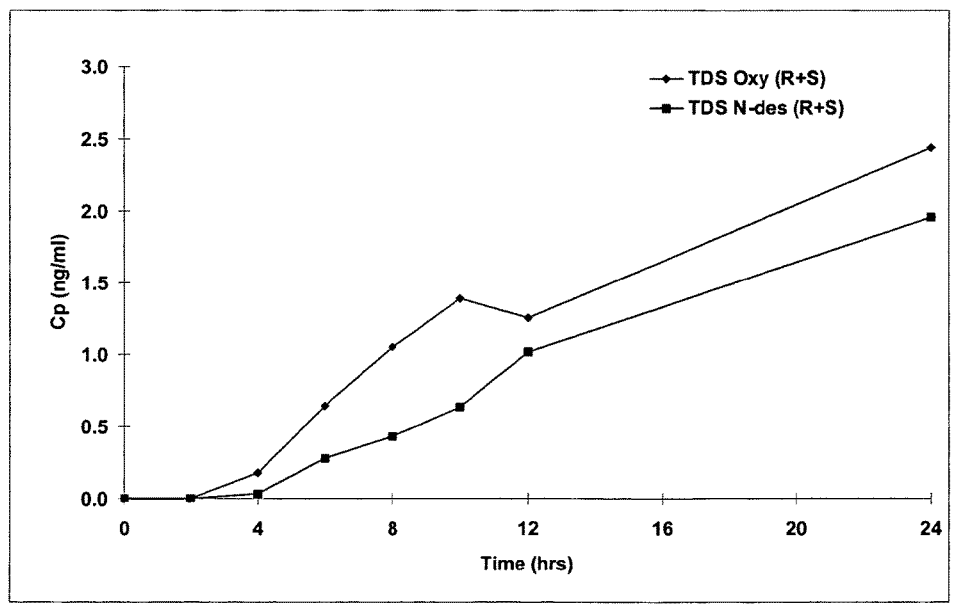
FIG. 2 is a graphical representation of total oxybutynin and N-desethyloxybutynin plasma concentrations measured upon transdermal administration according to the present invention, spanning a time from initial oxybutynin administration to 24 hours therefrom.

In describing and claiming the present invention, the following terminology will be used in accordance with the definitions set forth below.

The singular forms "a," "an," and, "the" include plural referents unless the context clearly dictates otherwise. Thus, for example, reference to "an adhesive" includes reference to one or more of such adhesives, and reference to "an excipient" includes reference to one or more of such excipients.

"Oxybutynin" refers to the compound having the general structure of:

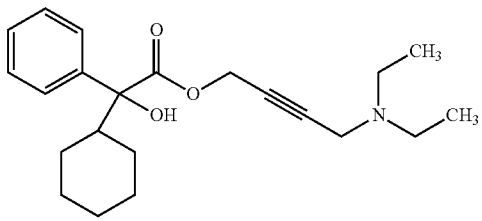 [SMILES: CCN(CC)CC#CCOC(=O)C(O)(c1ccccc1)C1CCCCC1]

The oxybutynin addition salt, oxybutynin HCl, is listed in the Merck Index, entry no. 7089, at page 1193, 12th ed., (1996, and is known by several IUPAC names such as a-Cyclohexyl-hydroxy-benzenacetic acid 4-(diethylamino)-2-butynyl ester hydrochloride; a-phenyl cyclohexanegly-colic acid 4-(diethylamino)-2-butynyl ester hydrochloride; and 4-di ethylamino-2-butynylphenylcyclohexylglycolate hydrochloride. "Oxybutynin" as used herein includes oxybutynin free base, its acid addition salts such as oxybutynin HCl, their analogs and related compounds, isomers, polymorphs, and prodrugs thereof. It is generally known that oxybutynin may exist in one or both of its isomeric forms, known as the (R)- and (S)-isomers, or a mixture of these two isomers. These isomeric forms and their mixtures are within the scope of this invention. Notably, in some portions of the present application, the context may clearly dictate the specific form of oxybutynin, such as oxybutynin chloride, even though only "oxybutynin" is recited.

"Administration," and "administering" refer to the manner in which a drug is presented to a subject. Administration can be accomplished by various art-known routes such as oral, parenteral, transdermal, inhalation, implantation, etc. Thus, an oral administration can be achieved by swallowing, chewing, sucking of an oral dosage form comprising the drug. Parenteral administration can be achieved by injecting a drug composition intravenously, intra-arterially, intramuscularly, intrathecally, or subcutaneously, etc. Transdermal administration can be accomplished by applying, pasting, rolling, attaching, pouring, pressing, rubbing, etc., of a transdermal preparation onto a skin surface. These and additional methods of administration are well-known in the art.

The term "non-oral administration" represents any method of administration in which a drug composition is not provided in a solid or liquid oral dosage form, wherein such solid or liquid oral dosage form is traditionally intended to substantially release and/or deliver the drug in the gastrointestinal tract beyond the mouth and/or buccal cavity. Such solid dosage forms include conventional tablets, capsules, caplets, etc., which do not substantially release the drug in the mouth or in the oral cavity.

It is appreciated that many oral liquid dosage forms such as solutions, suspensions, emulsions, etc., and some oral solid dosage forms may release some of the drug in the mouth or in the oral cavity during the swallowing of these formulations. However, due to their very short transit time through the mouth and the oral cavities, the release of drug from these formulations in the mouth or the oral cavity is considered deminimus or insubstantial. Thus, buccal patches, adhesive films, sublingual tablets, and lozenges that are designed to release the drug in the mouth are non-oral compositions for the present purposes.

In addition, it is understood that the term "non-oral" includes parenteral, transdermal, inhalation, implant, and vaginal or rectal formulations and administrations. Further, implant formulations are to be included in the term "non-oral," regardless of the physical location of implantation. Particularly, implantation formulations are known which are specifically designed for implantation and retention in the gastrointestinal tract. Such implants are also considered to be non-oral delivery formulations, and therefore are encompassed by the term "non-oral."

The term "subject" refers to a mammal that may benefit from the administration of a drug composition or method of this invention. Examples of subjects include humans, and other animals such as horses, pigs, cattle, dogs, cats, rabbits, and aquatic mammals.

As used herein, the terms "formulation" and "composition" are used interchangeably. The terms "drug" and "pharmaceutical" are also used interchangeably to refer to a pharmacologically active substance or composition. These terms of art are well-known in the pharmaceutical and medicinal arts.

The term "transdermal" refers to the route of administration that facilitates transfer of a drug through a skin surface wherein a transdermal composition is administered to the skin surface.

The term "skin" or "skin surface" is meant to include not only the outer skin of a subject comprising one or more of epidermal layers, but also to include mucosal surfaces to which a drug composition may be administered. Examples of mucosal surfaces include the mucosa of the respiratory (including nasal and pulmonary), oral (mouth and buccal), vaginal, and rectal cavities. Hence the terms "transdermal" may encompass "transmucosal" as well.

The terms "enhancement", or "permeation enhancement," mean an increase in the permeability of the skin, to a drug, so as to increase the rate at which the drug permeates through the skin. Thus, "permeation enhancer" or simply "enhancer" refers to an agent, or mixture of agents that achieves such permeation enhancement.

An "effective amount" of an enhancer means an amount effective to increase penetration of a drug through the skin, to a selected degree. Methods for assaying the characteristics of permeation enhancers are well-known in the art. See, for example, Merritt et al., Diffusion Apparatus for Skin Penetration, *J. of Controlled Release* 61 (1984), incorporated herein by reference in its entirety. By "effective amount" or "therapeutically effective amount," or similar terms is meant a non-toxic but sufficient amount of a drug, to achieve therapeutic results in treating a condition for which the drug is known to be effective. The determination of an effective amount is well-within the ordinary skill in the art of pharmaceutical and medical sciences. See for example, Curtis L. Meinert & Susan Tonascia, *Clinical Trials: Design, Conduct, and Analysis*, Monographs in Epidemiology and Biostatistics, vol. 8 (1986).

By the term "mean," "mathematical mean," "average," or similar terms when used in conjunction with the recitation of a number, or numbers, means the sum of all the individual observations or items of a sample divided by the number of items in the sample.

By the term "matrix", "matrix system", or "matrix patch" is meant a composition comprising an effective amount of a drug dissolved or dispersed in a polymeric phase, which may also contain other ingredients, such as a permeation enhancer and other optional ingredients. This definition is meant to include embodiments wherein such polymeric phase is laminated to a pressure sensitive adhesive or used within an overlay adhesive.

A matrix system may also comprise an adhesive layer having an impermeable film backing attached onto the distal surface thereof and, before transdermal application, a release liner on the proximal surface of the adhesive. The film backing protects the polymeric phase of the matrix patch and prevents release of the drug and/or optional ingredients to the environment. The release liner functions similarly to the impermeable backing, but is removed from the matrix patch prior to application of the patch to the skin as defined above. Matrix patches with the above-described general characteristics are known in the art of transdermal delivery. See, for example, U.S. Pat. Nos. 5,985,317, 5,783,208, 5,626,866, 5,227,169, which are incorporated by reference in their entirety.

"Topical formulation" means a composition in which the drug may be placed for direct application to a skin surface and from which an effective amount of the drug is released. Such formulations may include gels, lotions, cremes or other formulations which are applied to the skin. In some aspects, such formulations may be applied to the skin in an unoccluded form without additional backing, structures or devices.

As used herein, "unoccluded" and "non-occluded" may be used interchangeably, and refer to application of a topical formulation to the skin without the use of a supporting or otherwise associated structure. In other words, the topical formulation is applied to the skin in a free form, which is sufficient to effect transdermal delivery of oxybutynin without the use of structures, such as a backing member, etc.

As used herein, "gel" refers to a composition including a compound of high molecular weight which acts as a thickening agent to produce a semisolid or suspension-type formulation. The thickening or gelling agents may be hydrophobic or hydrophilic and are generally polymeric in nature. Gels which incorporate hydrophilic polymers are typically known in the art as hydrogels. Gels may include a variety of additional components such as, but not limited to, active agents, excipients, solvents, emulsifiers, chelating agents, surfactants, emollients, permeation enhancers, preservatives, antioxidants, lubricants, pH adjusters, adjuvants, dyes, and perfumes.

"Adverse drug experience" refers to any adverse event associated with the use of a drug in a subject, including the following: an adverse event occurring in the course of the use of a drug product in professional practice; an adverse event occurring from drug overdose whether accidental or intentional; an adverse event occurring from drug abuse; an adverse event occurring from drug withdrawal; and any failure of expected pharmacological action. The adverse drug experience may lead to a substantial disruption of a person's ability to conduct normal life functions. In some instances, the adverse drug experience may be serious or life threatening.

While some of the adverse drug experiences may be expected, in some instances, such experiences may be unexpected. "Unexpected," refers to an adverse drug experience that has not been previously catalogued by a responsible governmental agency (such as the Food and Drug Administration of the United States) and/or not provided in the current labeling for the drug product.

The unexpected adverse experiences may include events that may be symptomatically and pathophysiologically related to a known event, but differ from the event because of greater severity or specificity. For example, under this definition, hepatic necrosis would be unexpected (by virtue of greater severity) if the known event is elevated hepatic enzymes or hepatitis. Similarly, cerebral thromboembolism and cerebral vasculitis would be unexpected (by virtue of greater specificity) if the known event is cerebral vascular accidents. For a more comprehensive definition and description of adverse drug experience, see 21 C.F.R. § 314.80, which is incorporated by reference in its entirety.

The majority of the adverse experiences associated with oxybutynin therapy may be categorized as anticholinergic, and/or antimuscarinic. Certain adverse experiences associated with oxybutynin have been categorized in the Physician's Desk Reference as cardiovascular experiences, gastrointestinal/genitourinary experiences, dermatologic experiences, nervous system experiences, and ophthalmic experiences, among others.

Examples of cardiovascular adverse experiences include but are not limited to: palpitations, tachycardia, vasodilation, and combinations thereof. Examples of dermatologic adverse experiences include but are not limited to: decreased sweating, rashes, and combinations thereof. Examples of gastrointestinal/genitourinary adverse experiences include but are not limited to: constipation, decreased gastrointestinal motility, dry mouth, nausea, urinary hesitance and retention, and combinations thereof. Examples of nervous system adverse experiences include but are not limited to: asthenia, dizziness, drowsiness, hallucinations, insomnia, restlessness, and combinations thereof. Examples of ophthalmic adverse experiences include but are not limited to: amblyopia, cycloplegia, decreased lacrimation, mydriasis, and combinations thereof. Examples of other adverse experiences include but are not limited to: impotence and suppression of lactation. A more comprehensive listing of adverse experiences may be found in the labeling of the oxybutynin formulations as provided by the regulatory agencies.

The term "minimize" and its grammatical equivalents refer to a reduction in the frequency and/or severity of one or more adverse drug experiences in a given subject or subject population. It is appreciated that the subject population may be of necessity much smaller in size than the general population that may be exposed to the drug and/or its adverse experiences.

It is also appreciated that the results obtained from methods for determining the reduction in the frequency and/or severity of adverse drug experiences may be subject to variables such as intra-subject and inter-subject factors. However, it is also appreciated that certain scientifically accepted methods can be used to conduct the studies and that the results from such studies are statistically reliable. Such methods and interpretation of the results from such methods are well-known in the art. See, for example, Robert R. Sokal & F. James Rohlf, *Biometry: The Principles and Practice of Statistics in Biological Research*, $2^{nd}$ ed. (1969), which is incorporated by reference in its entirety.

The phrase "area under the curve", "area under the plasma concentration-time curve," or similar terms are well known in the pharmaceutical arts. These values are calculated by plotting a graph with data from plasma concentration of a given drug or its metabolites as a function of time, with the X-axis generally representing time and the Y-axis generally representing plasma concentration. The area under the line formed by joining the various data points is then integrated into a numerical value. See for example, Milo Gibaldi & Donald Perrier, *PharmacoKinetics*, 2$^{nd}$ ed. (1982). The AUC multiplied by the clearance or total body clearance (CL), of the substance being measured, thus provides an estimate of the total amount, or dose, of the substance being measured (the drug or one or more of its metabolites). Plasma concentrations, AUC, and CL may be subject to inter- and intra-subject variation due to physiological and/or environment factors present in individual subjects during the administration of medicinal agents, such as oxybutynin, in various formulation and/or compositions. Therefore, individual and mean values may be subject to variability, however, the general trends and relationships are preserved and reproducible.

Concentrations, amounts, solubilities, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited.

For example, a concentration range of 0.1 to 5 ng/ml should be interpreted to include not only the explicitly recited concentration limits of 0.1 ng/ml and 5 ng/ml, but also to include individual concentrations such as 0.2 ng/ml, 0.7 ng/ml, 1.0 ng/ml, 2.2 ng/ml, 3.6 ng/ml, 4.2 ng/ml, and sub-ranges such as 0.3-2.5 ng/ml, 1.8-3.2 ng/ml, 2.6-4.9 ng/ml, etc. This interpretation should apply regardless of the breadth of the range or the characteristic being described.

B. The Invention

As described above, the present invention provides compositions and methods for administering oxybutynin. These compositions and methods are shown to have minimized the incidence and/or severity of an adverse experience associated with oxybutynin administration, while providing sufficient oxybutynin to impart a therapeutic benefit. Without intending to be bound to any specific theory, it is believed that the minimization of adverse experiences is due in part to the reduction in plasma concentration of metabolites of oxybutynin such as N-desethyloxybutynin by the present compositions and methods when compared to conventional oral administration. The phrase "conventional oral administration" is meant to include the oral formulations as defined supra, and includes for example, an immediate-release or sustained-release oral tablet comprising oxybutynin. One such conventional oral formulation is available as a 5 mg immediate-release oral tablet.

1) The Pharmacokinetic Aspects Associated with Total Drug and Metabolite Plasma Concentrations The desired pharmacokinetic attributes such as reduced plasma concentrations of oxybutynin metabolites may be achieved by, inter alia: 1) reducing the amount of oxybutynin administered, 2) reducing the rate at which oxybutynin becomes available for metabolism by the body, and/or 3) avoiding or minimizing first-pass hepatic and/or intestinal metabolism of oxybutynin. Using a non-oral route of administration is one way to achieve one or more of these objectives. Alternatively, an oral dosage form could be designed to mimic a non-oral administration to achieve the plasma concentrations and other pharmacokinetic data described herein.

A clinical study has been performed to demonstrate one embodiment of the present invention. A cross-over clinical study in 16 healthy volunteers was conducted to compare plasma concentrations and pharmacokinetics of oxybutynin and one of its metabolites, N-desethyloxybutynin, and their respective (R)- and (S)-enantiomeric components.

Conventional oral dosage forms of oxybutynin, such as the 5 mg oxybutynin tablet used in the present study produce significantly higher plasma concentrations of oxybutynin metabolites such as N-desethyloxybutynin as compared to the parent drug (See FIG. 1). The mean AUC ratio of metabolite to oxybutynin concentration is about 10:1 in the majority of cases, and is generally greater than about 5:1.

In contrast, when oxybutynin is administered in a non-oral, slow release composition, such as the transdermal composition embodiment of the present invention, the mean AUC ratio of the metabolite (N-desethyloxybutynin) to oxybutynin is much lower. Generally, the mean AUC ratio of oxybutynin metabolite (N-desethyloxybutynin) to oxybutynin is less than about 2:1. Further, in the majority of instances, the ratio is less than about 1.2:1, and often, the ratio is approximately 0.9:1. (See FIG. 3).

Additionally, the mean N-desethyloxybutynin plasma concentration is generally less than about 8 ng/ml, and in the majority of instances is less than about 5 ng/ml. Often the mean is less than about 3 ng/ml.

2) Pharmacokinetic Aspects of Isomers

The present inventors have investigated further into the aspects described above and have discovered that the present formulations and methods provide significantly reduced levels of particular isomers of certain oxybutynin metabolites and that these reduced levels of metabolite isomers correlate to the minimized adverse drug experiences described above.

It is generally known that oxybutynin exists as an (R)- or as an (S)-isomer or a combination thereof. Particularly, (R)-oxybutynin has been thought to be the more active of the two isomers, as indicated by animal pharmacological studies using isolated tissues. See for example, Kachur J F, Peterson J S, Carter J P, et al. *J. Pharm Exper. Ther.* 1988; 247:867-872; see also, Noronha-Blob L, Kachur J F. *J. Pharm. Exper. Ther.* 1990; 256:56-567. As such, (R)—N-desethyloxybutynin, being the more active constituent of the total amount of metabolite, may contribute more significantly to adverse drug experiences such as anticholinergic adverse effects than the less active (S)—N-desethyloxybutynin. See for example, U.S. Pat. No. 5,677,346, which is incorporated by reference in its entirety.

Accordingly, plasma concentrations were measured for both (R)- and (S)-oxybutynin and the corresponding isomers of one of its metabolites, N-desethyloxybutynin during the clinical study mentioned above. The tests performed revealed that the present invention results in significantly lower (R)—N-desethyloxybutynin plasma concentrations compared to conventional oral dosage forms and administration methods.

Figure 6:
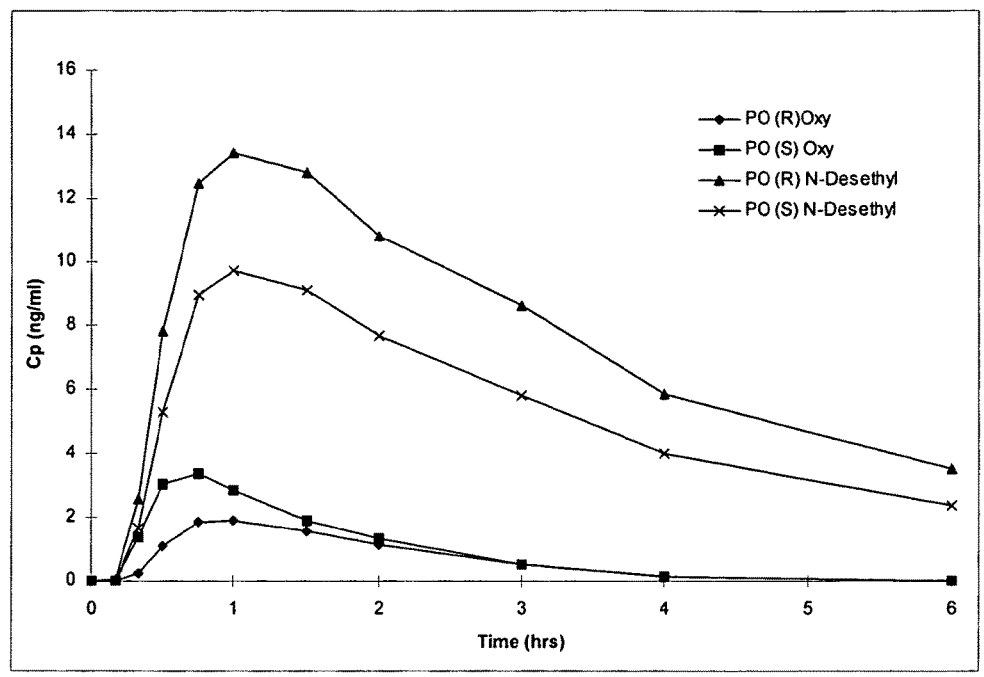
FIG. 6 is a graphical representation of the plasma concentrations produced for the (R) and (S) isomers of both oxybutynin and N-desethyloxybutynin upon administering a 5 mg immediate-release oral tablet.

FIG. 6 shows the plasma concentration profile from the conventional oxybutynin 5 mg oxybutynin oral tablet. As can be seen, (R)—N-desethyloxybutynin is present in the greatest concentration, and is several times the concentration of both (R)- and (S)-oxybutynin. The mean AUC ratio of the (R)—N-desethyloxybutynin to (R)-oxybutynin, the two most active isomers, following oral administration is about 17:1. In addition, the mean AUC ratio of (R)—N-desethyloxybutynin to (S)—N-desethyloxybutynin is about 1.5:1, and the mean AUC ratio of (R)-oxybutynin to (S)-oxybutynin is about 0.6:1. These ratios of AUC consistently show that orally administered oxybutynin results in a relatively low amount of therapeutically active (R)-oxybutynin given the large total dose of racemic oxybutynin. Further, the oral dose results in a relatively large amount of (R)—N-desethyloxybutynin, the moiety most likely to be responsible for causing some or many of the adverse drug experiences.

Figure 7:
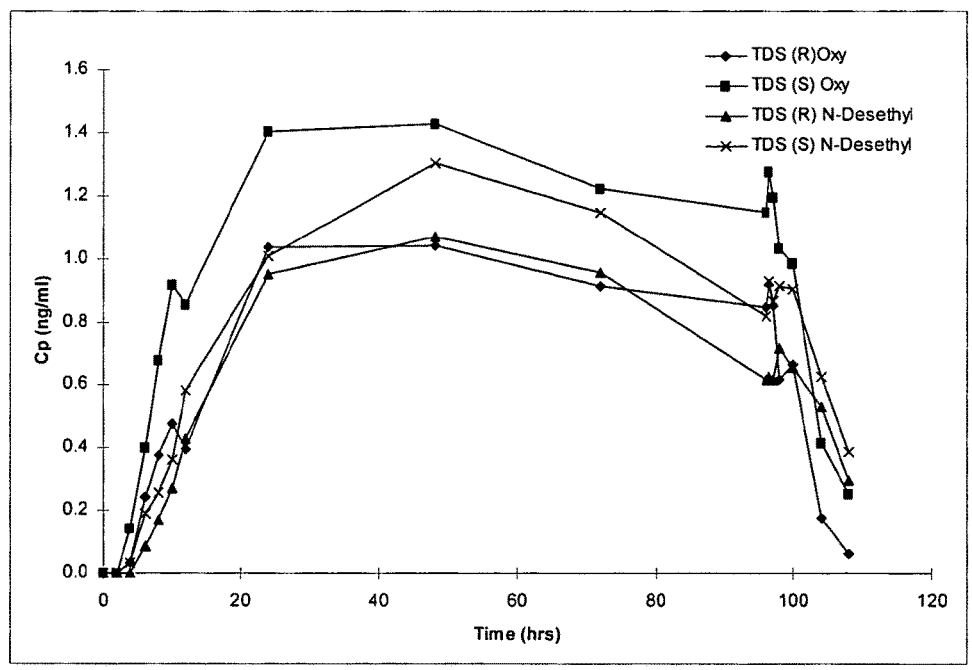
FIG. 7 is a graphical representation of the plasma concentrations of (R) and (S) isomers for both oxybutynin and N-desethyloxybutynin achieved by transdermal administration in accordance with the present invention.

In contrast, FIG. 7 shows the (R)- and (S)-isomer plasma profiles of the present invention which were achieved during the clinical study by non-orally delivered oxybutynin. The mean AUC ratio of (R)-oxybutynin to (S)-oxybutynin is about 0.7:1, and the sustained plasma concentrations of (R)-oxybutynin are similar to the peak concentrations obtained following oral administration. This comparable exposure to the therapeutically active (R)-oxybutynin moiety is consistent with the invention.

Thus, with transdermal administration, it has been discovered that: the mean AUC ratio of (R)—N-desethyloxybutynin to (R)-oxybutynin is lowered, resulting in greatly reduced amounts of the active metabolites of oxybutynin, while providing a therapeutically effective amount of oxybutynin.

Figure 4:
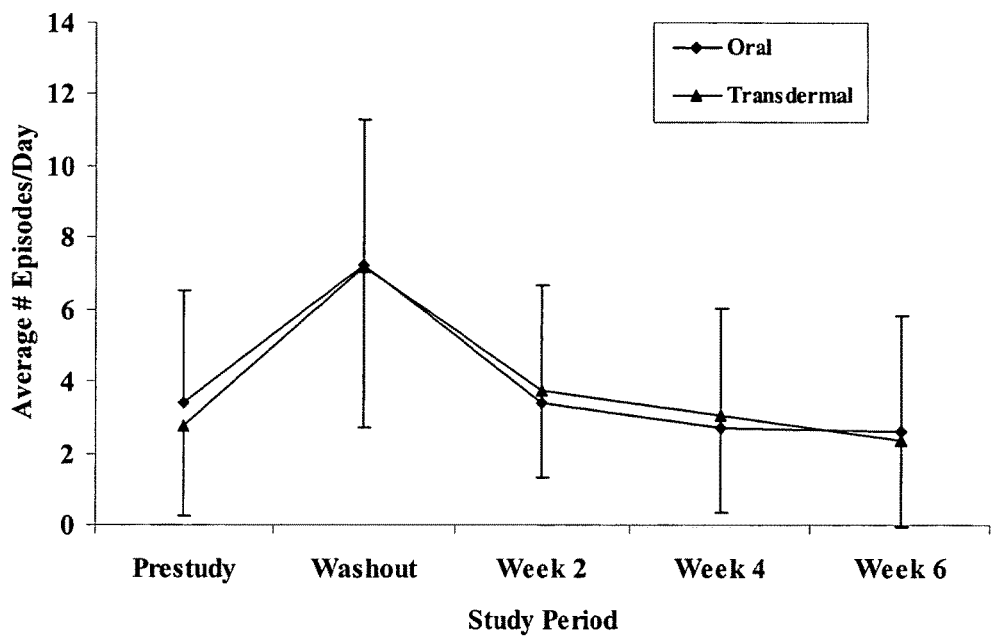
FIG. 4 is a graphical representation of the results of treating a subject with overactive bladder with transdermal administration of oxybutynin in accordance with the present invention, as compared to treatment with a 5 mg immediate-release oxybutynin oral tablet by recording the number of episodes of urinary incontinence.
Figure 5:
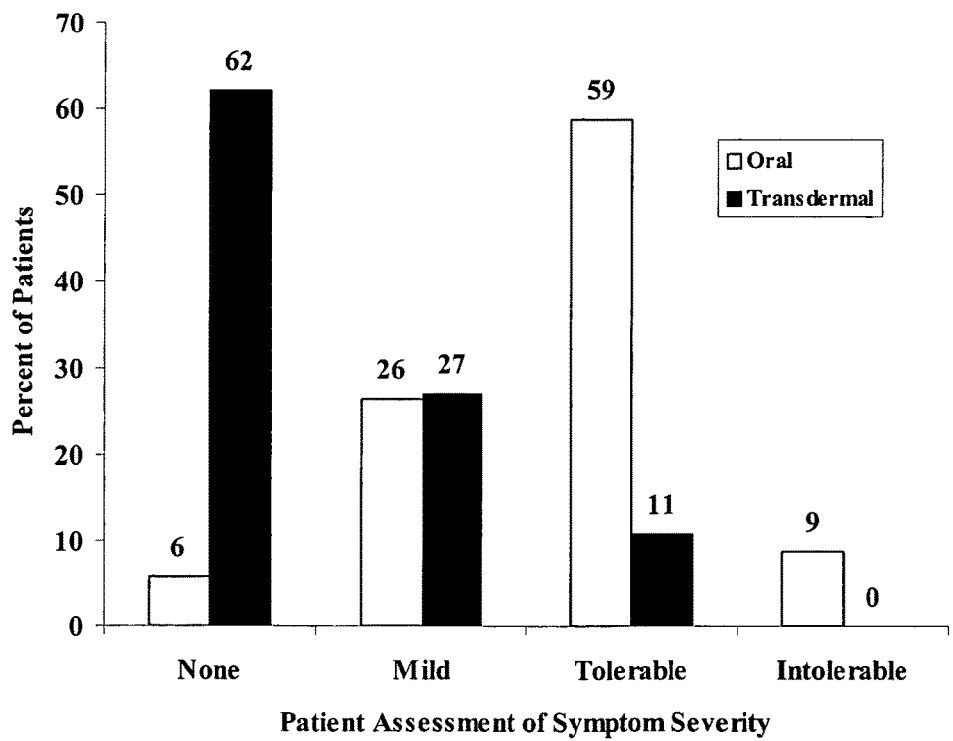
FIG. 5 is a graphical representation of the anticholinergic adverse experiences reported by subjects receiving treatment for overactive bladder with a transdermal administration of oxybutynin in accordance with the present invention, as compared to treatment with a 5 mg oxybutynin immediate-release oral tablet.

By comparing FIGS. 4, 5, and 7, it becomes clear that the present compositions and methods provide an optimal ratio of plasma concentrations of metabolites, such as (R)—N-desethyloxybutynin, to oxybutynin, such that these methods and compositions minimize adverse experiences associated with oxybutynin administration, as compared to traditional oral formulations, while maintaining therapeutically sufficient concentrations of (R)-oxybutynin to provide the benefits of oxybutynin therapy. As indicated above, these compositions and methods offer a significant advancement in oxybutynin therapy.

3) Therapeutic Aspects

A clinical study on the efficacy and minimization of incidence and severity of adverse drug experiences associated with non-orally administered oxybutynin was conducted using 72 human subjects (patients) with overactive bladder. Approximately one-half of the patients were administered oxybutynin hydrochloride in an oral dosage formulation. The remaining patients were administered oxybutynin using a non-oral route of delivery such as a transdermal adhesive matrix patch over a period of about 6 weeks. The results are displayed graphically in FIGS. 4 and 5.

The non-oral, sustained-release composition of this invention was compared for its therapeutic efficacy with the conventional 5 mg oral tablet of oxybutynin. The mean number of incontinent episodes experienced per day as derived from a multiple-day patient urinary diary was used as the desired therapeutic efficacy indicator. The data show that the number of incontinent episodes for those individuals treated by the non-oral method of the present invention is nearly identical to the number for those treated with the oral formulation. (See FIG. 4).

Next, the non-oral sustained-release formulation of the present invention was compared to the conventional immediate-release oral tablet for the incidence and severity of adverse drug experiences. The adverse experience of dry mouth was selected as an indicator for this experiment. As can be seen, only 6% of the participants who received the conventional oral oxybutynin tablet reported no dry mouth effects. Conversely, 94% of these participants reported experiencing some dry mouth.

In contrast, 62% of the participants who were treated with the transdermal adhesive matrix patch of the present invention reported no dry mouth effects. Therefore, only 38% of these participants reported experiencing some dry mouth, and none rated the dry mouth as intolerable.

These data show that the adverse experiences associated with oxybutynin administration can be minimized significantly, while fully retaining the therapeutic efficacy of oxybutynin by administering oxybutynin such that an optimal ratio of AUC of oxybutynin metabolite to oxybutynin results.

4) Summary of Pharmacokinetic Aspects of the Invention

From the above-described pharmacokinetic data, the following aspects of the invention can be presented. In one aspect, the mean peak plasma concentration of an oxybutynin metabolite is less than about 8 ng/ml. In another aspect, the mean peak plasma concentration of the metabolite is from about 0.5 ng/ml to about 8 ng/ml; in yet another aspect, the concentration is less than about 5 ng/ml; in yet another aspect, the concentration is from about 1.0 ng/ml to about 3 ng/ml. In some aspects, the metabolite of oxybutynin is N-desethyloxybutynin.

In some aspects, the mean oxybutynin metabolite AUC is reduced to an amount which does not exceed the oxybutynin AUC by more than a ratio of about 2:1. In some aspects, the mean oxybutynin metabolite AUC is reduced to less than about 0.9:1 ng/ml.

In some aspects, the present invention provides compositions and methods for administering oxybutynin to a subject such that the mean AUC ratio of oxybutynin to an oxybutynin metabolite is about 0.5:1 to about 5:1. In some aspects, the ratio is from about 0.5:1 to about 4:1; in some other aspects, the ratio is from about 1:1 to about 5:1; in yet other aspects, the ratio is from about 0.8:1 to about 2.5:1; in yet some other aspects, the ratio is from about 0.8:1 to about 1.5:1. In all the above aspects, the metabolite may be N-desethyloxybutynin.

Another way of characterizing the method of the present invention is by specifying particular plasma concentrations for oxybutynin and metabolite concentrations at certain time intervals following treatment initiation. Therefore, in one aspect, oxybutynin plasma concentrations are below about 2.0 ng/ml at about 6 hours after oxybutynin treatment initiation. In another aspect, the metabolite plasma concentrations are also below about 2.0 ng/ml at about 6 hours after treatment initiation.

In yet another aspect, oxybutynin and its metabolite plasma concentrations are below about 8 ng/ml at about 24 hours after initial oxybutynin administration. Further, mean steady state oxybutynin and its metabolite plasma-concentrations are below about 8 ng/ml for the duration of oxybutynin treatment.

In one aspect, the mean peak and mean AUC for (R)—N-desethyloxybutynin are about equal to or less than the mean peak, and mean AUC for (S)—N-desethyloxybutynin. In another aspect, the mean AUC ratio of (R)—N-desethyloxybutynin to (S)—N-desethyloxybutynin is about 0.9:1. In yet another aspect, the mean peak and mean AUC for (R)-oxybutynin are approximately equal to (R)—N-desethyloxybutynin. In another aspect, the ratio of (R)—N-desethyloxybutynin to (S)—N-desethyloxybutynin is about 1:1.

In an additional aspect, (R)—N-desethyloxybutynin has a mean peak plasma concentration of less than about 4 ng/mL. In another aspect, (R)—N-desethyloxybutynin has a mean peak plasma concentration between about 0.25 to about 4 ng/ml, and about 1.5 ng/ml.

In a one aspect, (R)—N-desethyloxybutynin has a mean AUC of about 100 ng×hr/ml. In another aspect, (R)—N-desethyloxybutynin has a mean AUC from about 30 ng×hr/ml to about 170 ng×hr/ml.

In yet another aspect, the plasma concentration of (R)—N-desethyloxybutynin is below about 1 ng/ml at about 6 hours after initiation of oxybutynin administration. In a further aspect, the plasma concentration of (R)—N-desethyloxybutynin is below about 2 ng/ml at about 24 hours after initiation of oxybutynin administration.

Therapeutic oxybutynin plasma concentrations vary based on the severity of incontinence. Generally, therapeutic results may be obtained from oxybutynin plasma concentrations as low as 0.5 ng/ml. Therapeutic blood levels may be achieved using the method of the present invention in as little as 3 hours after treatment initiation, with peak oxybutynin plasma concentrations being reached in about 24 hours. However, these general parameters are not limitations on the way in which the desired plasma levels may be achieved. Different delivery methods, rates, and amounts may be used to effect the desired plasma concentrations by employing a formulation which produces different parameters.

5) Composition Aspects

Any pharmaceutically acceptable compositions and methods for administering such compositions may be used for achieving the desired aspects of this invention. For example, oral and non-oral compositions and methods of administration can be used. Non-oral compositions and methods of administration include parenteral, implantation, inhalation, and transdermal compositions and methods.

Oral compositions and administrations can comprise of slow-release compositions that are designed to mimic the non-oral compositions and administrations that are specifically disclosed herein in terms of their pharmacokinetic attributes described above. One of ordinary skill in the art would readily understand how to formulate and administer such slow-release oral formulations. These formulations can take the form of a tablet, capsule, caplet, pellets, encapsulated pellets, etc., or a liquid formulation such as a solution or suspension. See, for example, U.S. Pat. No. 5,840,754, and WO 99/48494 which are incorporated by reference in their entirety.

Parenteral compositions and administrations may include intravenous, intra-arterial, intramuscular, intrathecal, subcutaneous, etc. These compositions can be prepared and administered to provide slow-release of oxybutynin to achieve the pharmacokinetic profile and therapeutic benefits described above. One specific example of preparing a depot-formulation for parenteral use is provided herein. General methods for preparing sustained delivery of drugs for parenteral use comprising microspheres are known in the art. See for example, U.S. Pat. Nos. 5,575,987, 5,759,583, 5,028,430, 4,959,217, and 4,652,441, which are incorporated by reference in their entirety.

Implantation is a technique that is well-established to provide controlled release of drugs over a long period of time. Several subcutaneously implantable devices have been disclosed in the art. See for example, U.S. Pat. Nos. 5,985, 305, 5,972,369, and 5,922,342, which are incorporated by reference in their entirety. By employing these general techniques, one of ordinary skill in the art can prepare and administer implantable oxybutynin compositions to achieve the pharmacokinetic and therapeutic benefits of this invention.

Examples of oxybutynin transdermal administration formulations include but are not limited to: 1) topical formulations such as ointments, lotions, gels, pastes, mousses, aerosols, and skin creams; 2) transdermal patches such as adhesive matrix patches and liquid reservoir systems. Other non-oral examples include transmucosal tablets such as buccal, or sublingual tablets or lozenges, and suppositories.

In addition to the desired amount of oxybutynin, transdermal oxybutynin formulations may also include a permeation enhancer, or mixture of permeation enhancers in order to increase the permeability of the skin to oxybutynin. An index of permeation enhancers is disclosed by David W. Osborne and Jill J. Henke, in their publication entitled *Skin Penetration Enhancers Cited in the Technical Literature*, published in "Pharmaceutical Technology" (June 1998), which may also be found at the worldwide web address known as: pharmtech.com/technical/osborne/osborne.htm, which is incorporated by reference herein.

More particularly, permeation enhancers known to enhance the delivery of oxybutynin include but are not limited to: fatty acids, fatty acid esters, fatty alcohols, fatty acid esters of lactic acid or glycolic acid, glycerol tri-, di- and monoesters, triacetin, short chain alcohols, and mixtures thereof. Specific species or combinations of species may be selected from the above listed classes of compounds by one skilled in the art, in order to optimize enhancement of the particular oxybutynin composition employed.

The transdermal formulation of the present invention may take the form of a non-occlusive topical formulation, such as a gel, ointment such as a lotion, cream or paste, or an occlusive device such as a transdermal patch. A transdermal patch in accordance with the present invention may either be an adhesive matrix patch, a liquid reservoir system type patch, a buccal tablet, or the like. Optional ingredients such as adhesives, excipients, backing films, etc, and the required amount of each will vary greatly depending upon the type of patch desired, and may be determined as needed by one ordinarily skilled in the art. Methods for preparing and administering the transdermal formulations with the above-described characteristics are known in the art. See, for example, U.S. Pat. Nos. 5,762,953, and 5,152,997, which are incorporated by reference in their entirety.

In one aspect of the present invention, a free form oxybutynin ointment may be prepared for topical administration in accordance with the discussion herein. An ointment is a semisolid pharmaceutical preparation based on a well known materials such as an oleaginous base, lanolin, emulsions, or water-soluble bases. Preparation of ointments is well known in the art such as described in Remington, supra, vol. 2, pp. 1585-1591. Such preparations often contain petrolatum or zinc oxide together with an active agent. Oleaginous ointment bases suitable for use in the present invention include generally, but are not limited to, vegetable oils, animal fats, and semisolid hydrocarbons obtained from petroleum. Absorbent ointment bases of the present invention may contain little or no water and may include components such as, but not limited to, hydroxystearin sulfate, anhydrous lanolin and hydrophilic petrolatum. Emulsion ointment bases of the present invention are either water-in-oil (W/O) emulsions or oil-in-water (O/W) emulsions, and may include, but are not limited to, cetyl alcohol, glyceryl monostearate, lanolin, polyalkylsiloxanes, and stearic acid. Water-soluble ointment bases suitable for use in the present invention may be prepared from polyethylene glycols of varying molecular weight.

In an additional aspect, ointments of the present invention may include additional components such as, but not limited to, additional active agents, excipients, solvents, emulsifiers, chelating agents, surfactants, emollients, permeation enhancers, preservatives, antioxidants, lubricants, pH adjusters, adjuvants, dyes, and perfumes. The specific choice and compositions of such additional components may be made by those skilled in the art in accordance with the principles of the present invention.

In another aspect of the present invention, a free form oxybutynin cream may be prepared in accordance with the principles of the present invention. Creams are a type of ointment which are viscous liquids or semisolid emulsions, either oil-in-water or water-in-oil, as is well known in the art. Cream bases may be soluble in water, and contain an oil phase, an emulsifier, an aqueous phase, and the active agent. In a detailed aspect of the present invention, the oil phase may be comprised of petrolatum and a fatty alcohol such as cetyl or stearyl alcohol. In another detailed aspect of the present invention, the aqueous phase may exceed the oil phase in volume, and may contain a humectant. In another detailed aspect of the present invention, the emulsifier in a cream formulation may be a nonionic, anionic, cationic or amphoteric surfactant.

In a more detailed aspect of the present invention, the free form oxybutynin cream is an oil-in-water emulsion. The water phase of the oxybutynin cream may contain between about 20 and about 60% w/w of water, between about 1 and about 15% w/w of at least one emulsifier, up to about 50% w/w of an oil phase, and up to about 1% w/w of a preservative such as a paraben. The oil phase of the free form oxybutynin cream may contain up to about 40% w/w of a solvent, up to about 15% w/w of at least one emulsifier, up to about 40% w/w of an oil phase, and up to about 1% w/w of a preservative such as a paraben.

In another aspect of the present invention, a free form oxybutynin lotion may be prepared in accordance with the principles of the present invention. A lotion is an ointment which may be a liquid or semi-liquid preparation in which solid particles, including the active agent, are present in a water or alcohol base. Lotions suitable for use in the present invention may be a suspension of solids or may be an oil-in-water emulsion. In another aspect of the present invention, lotions may also contain suspending agents which improve dispersions or other compounds which improve contact of the active agent with the skin, e.g., methylcellulose, sodium carboxymethylcellulose, or similar compounds.

In an additional aspect, oxybutynin lotions of the present invention may include additional components such as, but not limited to, additional active agents, excipients, solvents, emulsifiers, chelating agents, surfactants, emollients, permeation enhancers, preservatives, antioxidants, lubricants, pH adjusters, adjuvants, dyes, and perfumes. The specific choice and compositions of such additional components may be made by those skilled in the art in accordance with the principles of the present invention and may differ from the components which would be chosen for other topical formulations of the present invention.

In another more detailed aspect of the present invention, free form oxybutynin lotions may be an emulsion of a water and oil phase. The water phase of the oxybutynin lotion may contain between about 20% w/w and about 90% w/w of an excipient such as water, up to about 5% w/w of a surfactant, up to about 5% w/w of sodium chloride or the like, and up to about 1% w/w of a preservative such as a paraben. The oil phase of the oxybutynin lotion may contain up to about 40% w/w of at least one solvent such as glycerin and cetyl alcohol, up to about 10% w/w of an absorbent base such as petrolatum, up to about 5% w/w of an antioxidant such as isopropyl palmitate, up to about 5% w/w of an oil phase such as dimethicone, and up to about 1% w/w of a preservative such as a paraben.

In yet another aspect of the present invention, a free form oxybutynin paste may be prepared in accordance with the present invention. Pastes of the present invention are ointments in which there are significant amounts of solids which form a semisolid formulation in which the active agent is suspended in a suitable base. In a detailed aspect of the present invention, pastes may be formed of bases to produce fatty pastes or made from a single-phase aqueous gel. Fatty pastes suitable for use in the present invention may be formed of a base such as petrolatum, hydrophilic petrolatum or the like. Pastes made from single-phase aqueous gels suitable for use in the present invention may incorporate cellulose based polymers such as carboxymethylcellulose or the like as a base.

In an additional aspect, oxybutynin pastes of the present invention may include additional components such as, but not limited to, additional active agents, excipients, solvents, emulsifiers, chelating agents, surfactants, emollients, permeation enhancers, preservatives, antioxidants, lubricants, pH adjusters, adjuvants, dyes, and perfumes.

In another aspect of the present invention, a free form oxybutynin gel may be prepared. An oxybutynin gel prepared in accordance with the present invention may be a preparation of a colloid in which a disperse phase has combined with a continuous phase to produce a viscous product. The gelling agent may form submicroscopic crystalline particle groups that retain the solvent in the interstices. As will be appreciated by those working in art, gels are semisolid, suspension-type systems. Single-phase gels can contain organic macromolecules distributed substantially uniformly throughout a carrier liquid, which may be aqueous or non-aqueous and may contain an alcohol or oil.

In another aspect, the transdermal formulation of the present invention may be a topical gel containing oxybutynin for unoccluded administration to the skin. A variety of specific gel vehicles are known to those of ordinary skill in the art. Examples of specific gel types, their manufacture and use may be found, for example, in U.S. Pat. Nos. 2,909,462; 4,340,706; 4,652,441; 5,516,808; 5,643,584; 5,840,338; 5,912,009; and 6,258,830, each of which are incorporated herein by reference in their entirety.

However, in some aspects, the gel formulation may be prepared by providing a gelling agent, usually in a powdered form, and adding an excipient such as water in the case of a hydrophilic gelling agent or mineral oil in the case of a hydrophobic gelling agent. The gel then swells and may be optionally neutralized. In a separate vessel, oxybutynin may be dissolved in an appropriate solvent. The dissolved oxybutynin and the gel may then be mixed to form the final gel formulation. Other methods of producing a drug-containing gel will be recognized by those of ordinary skill in the art.

Although gels used in reservoir devices may have similar components additional considerations may be important in designing a free form gel. For example, free form gels may offer a number of advantages, such as ease of administration, increased patient compliance, simple adjustment of dosage, decreased manufacturing costs, and reduced skin irritation. Moreover, certain excipients useful in effecting administration of oxybutynin may be included in a free form gel in greater amounts, than is possible in an occluded gel, such as in an LRS patch, due to performance factors such as skin irritation, etc.

In accordance with a more detailed aspect of the present invention, the free form gel may include a variety of additional components such as, but not limited to, additional active agents, excipients, solvents, emulsifiers, chelating agents, surfactants, emollients, permeation enhancers, preservatives, antioxidants, lubricants, pH adjusters, adjuvants, dyes, and perfumes. The additional components may be added to the dissolved oxybutynin either before or after combination with the gel. Further, in order to prepare a uniform gel, dispersing agents such as alcohol or glycerin can be added, or the gelling agent can be dispersed by trituration, mechanical mixing or stirring, or combinations thereof. It will be recognized, however, by those skilled in the art that other methods and means of incorporating the oxybutynin and other components into the gel may be employed consistent with the teachings of the present invention.

In accordance with the present invention, the free form gel may be aqueous or non-aqueous based. In either case, the formulation should be designed to deliver the oxybutynin in accordance with the release rates and blood plasma concentrations recited herein. In one aspect of the present invention, aqueous gels may comprise water or water/ethanol and about 1-5 wt % of a gelling agent. In another aspect of the present invention, non-aqueous gels may be comprised of silicone fluid, such as colloidal silicon dioxide, or mineral oil. The suitability of a particular gel depends upon the compatibility of its constituents with both the oxybutynin and the permeation enhancer, if used, and any other components in the formulation.

In accordance with the present invention, oxybutynin used in the free form gel may be provided as the oxybutynin free base, its acid addition salts such as oxybutynin HCl, their analogs and related compounds, isomers, polymorphs, prodrugs, optically pure (R) or (S) isomers, racemic mixture and combinations thereof. The oxybutynin may be provided in a micronized form or other powdered form. In one aspect of the present invention, the oxybutynin is present at about 0.1 wt % to about 10 wt % of the free form gel. In accordance with one aspect of the present invention, the oxybutynin may be present between about 5 and about 20 mg/gram.

In accordance with the present invention, the gelling agent may be a compound of high molecular weight which acts as a thickening agent to produce a semisolid or suspension-type formulation. As mentioned above, gelling agents may be hydrophobic or hydrophilic and are generally polymers. Gels which incorporate hydrophilic polymers are referred to as hydrogels, as is understood by those skilled in the art.

Examples of suitable gelling agents for use in the present invention may include synthetic polymers such as, but not limited to, polyacrylic acids or poly(1-carboxyethylene), carboxypolymethylenes prepared from acrylic acid cross-linked with allyl ethers of (polyalkyl) sucrose or pentaerythritol (e.g. CARBOPOL 940/941/980/981/1342/1382 and carbomer polymers such as carbomer 934P/974P), sodium acrylate polymers (e.g. AQUAKEEP J-550/J-400), other polycarboxylic acids, alkyl acrylate polymers (e.g. PEMULEN), and mixtures or copolymers thereof. In another aspect of the present invention, the gelling agent is a CARBOPOL. In one more detailed aspect of the present invention, the gelling agent is an alkyl acrylate polymer. In yet another aspect of the present invention, the gelling agent is a mixture of CARBOPOL and an alkyl acrylate polymer.

In another aspect of the present invention, suitable gelling agents may include vinyl polymers such as but not limited to carboxyvinyl polymers, polyvinyl pyrrolidone, polyvinyl alcohol, polyvinyl methyl ether, polyvinyl ether, polyvinyl sulfonates, and mixtures or copolymers thereof.

In a further aspect of the present invention, suitable gelling agents may include polymers such as but not limited to polyethylene compounds (e.g. polyethylene glycol, etc.), polysaccharides (e.g. polysucrose, polyglucose, polylactose, etc.) and salts thereof, acrylic acid esters, alkoxybutynin- polymers (e.g. polyoxyethylene-polyoxypropylene copolymers such as the PLURONIC line of BASF, Parsippany, N.J.), polyethylene oxide polymers, polyethers, gelatin succinate, colloidal magnesium aluminum silicate (which may be useful as a gel stabilizer in conjunction with another gelling agent), petroleum jelly and mixtures of copolymers thereof.

Suitable gelling agents also include cellulose polymers such as hydroxypropyl cellulose (e.g. KLUCEL), hydroxypropylmethyl cellulose (e.g. KLUCEL HF, METHOCEL), hydroxypropylethyl cellulose, hydroxypropylbutyl cellulose, hydroxypropylpentyl cellulose, hydroxyethyl cellulose (NATROSOL), ethylcellulose, carboxymethyl cellulose, hydroxypropylmethyl cellulose phthalate, and cellulose acetate. In one more detailed aspect of the present invention, the gelling agent is hydroxypropyl cellulose. In a more detailed aspect of the present invention, the gelling agent is hydroxyethyl cellulose. In yet another aspect of the present invention, the gelling agent is a mixture of hydroxyethyl cellulose and an alkyl acrylate polymer. In a further aspect of the present invention, the gelling agent is a mixture of hydroxypropyl cellulose and a CARBOPOL.

In yet another more detailed aspect of the present invention, suitable gelling agents may be natural gelling agents include, dextran, gaur-gum, tragacanth, xanthan gum, sodium alginate, sodium pectinate, sodium alginate, acacia gum, Irish moss, karaya gum, guaiac gum, locust bean gum, etc., while natural high molecular weight compounds include, among others, various proteins such as casein, gelatin, collagen, albumin (e.g. human serum albumin), globulin, fibrin, etc. and various carbohydrates such as cellulose, dextrin, pectin, starches, agar, mannan, and the like. These substances may be also be chemically modified, e.g. esterified or etherified forms, hydrolyzed forms (e.g. sodium alginate, sodium pectinate, etc.) or salts thereof.

The amount of gelling agent employed in a gel of the present invention may vary depending on the specific result to be achieved. However, in one aspect, the amount of gelling agent may be from about 0.05 to about 10 wt % of the gel formulation. In a more detailed aspect, the amount of gelling agent may be 0.1 to 5 wt % of the gel formulation prior to introduction of the dissolved oxybutynin and any accompanying components. In yet a more detailed aspect, the free form gel may contain about 0.1 to about 3 wt % of a gelling agent in the gel formulation.

In another aspect of the present invention, solvents or solubilizing agents may also be used in the free form gel. Such solvents may be necessary when the drug is not soluble in the chosen gelling agent. Suitable solvents for use in the present invention include, but are not limited to lower alcohols, ethanol, isopropanol, benzyl alcohol, propanol, methanol, other $C_4$-$C_{10}$ mono-alcohols and mixtures thereof. In another aspect the solvents suitable for use in the present invention may include albumin, gelatin, citric acid, ethylenediamine sodium tetraacetate, dextrin, DMSO, dimethylformamide, 2-pyrrolidone, N-(2-hydroxyethyl) pyrrolidone, N-methyl pyrrolidone, 1-dodecylazacycloheptan-2-one and other n-substituted-alkyl-azacycloalkyl-2-ones (azones), sodium hydrosulfite and mixtures thereof.

In one aspect, the ethanol may be present from about 60% to about 85% w/w of the formulation. In another aspect, the ethanol may be present from about 65% to about 80% w/w of the formulation. In another aspect, the ethanol may be present from about 70% to about 85% w/w of the formulation. In another aspect, the ethanol may be present from about 70% to about 75% w/w of the formulation.

In one aspect, the water may be present from about 1% to about 30% w/w of the formulation. In another aspect, the water may be present from about 5% to about 30% w/w of the formulation. In another aspect, the water may be present from about 5% to about 20% w/w of the formulation. In yet another aspect, the water may be present from about 10% to about 30% w/w of the formulation. In another aspect, the water may be present from about 10 to about 25% w/w of the formulation. In yet another aspect, the water may be present from about 10% to about 20% w/w of the formulation. In yet another aspect, the water may be present from about 15% to about 25% w/w of the formulation. In another aspect, the water may be present from about 20% to about 25% w/w of the formulation.

Those of ordinary skill in the art will appreciate that the specific amount and type of solvent selected may be determined based on a specific result to be achieved. However, in one aspect, the amount of solvent may be at least about 25% w/w of the formulation. In another aspect, the amount of solvent may be at least about 30% w/w of the formulation. In a further aspect, the amount of solvent may be at least about 40% w/w of the formulation. In an additional aspect, the amount of solvent may be at least about 70% w/w of the formulation.

In yet a more detailed aspect of the present invention, excipients such as, but not limited to, water, mineral oils, or silicon fluids may also be added and are largely dependent on the chosen gelling agent. The excipient may comprise a substantial portion of the gel formulation, i.e. greater than about 50%. In one aspect of the present invention, the free form gel contains excipient in an amount from 0% to about 75%.

In yet another more detailed aspect of the present invention, an emulsifier may also be used particularly when solvent is used. Emulsifiers suitable for use in the present invention include, but are not limited to, polyols and esters thereof such as glycols, propylene glycol, polyethylene glycol, glycolhexylene glycol, ethylene glycol, glycerol, butanediol, polyethylene glycol monolaurate, and propylene glycol ester of alginic acid. Emulsification may be accomplished by conventional dispersion techniques. For example, intermittent shaking, mixing by means of a propeller mixer, turbine mixer or the like, colloid mill operation, mechanical homogenization, ultrasonication, or other known methods may be utilized. Emulsifiers may form stable oil-in-water emulsion, and such emulsifiers are exemplified by anionic surfactants (e.g. sodium oleate, sodium stearate, sodium laurylsulfate, etc.), nonionic surfactants (e.g. polyoxyethylene sorbitan fatty acid esters (Tween 80 and Tween 60, Atlas Powder, U.S.A.), polyoxyethylene castor oil derivatives (HCO-60 and HCO-50, Nikko Chemicals, Japan], etc.), polyvinyl pyrrolidone, polyvinyl alcohol, carboxymethylcellulose, lecithin, gelatin, and combinations thereof. The concentration of the emulsifier may be selected from the range of about 0.01% to about 20%. It will be noted that many of these emulsifiers also act as gelling agents.

In another aspect of the present invention, a chelating agent may be used to prevent precipitation or decomposition of the oxybutynin. Suitable chelating agents for use in the present invention may include, but are not limited to, sodium and calcium salts of EDTA, and edetate disodium.

In yet a more detailed aspect of the present invention, surfactants may be desirable since the inclusion of a surfactant may have the dual benefit of helping to maintain the active ingredient in uniform suspension in the gel formulation, while enhancing the bio-availability of the oxybutynin. Further, many surfactants also act as permeation enhancers.

Surfactants suitable for use in the present invention may include, but are not limited to, lecithin; sorbitan monoesters, such as sorbitan monooleate, sorbitan monolaurate, sorbitan monopalmitate, sorbitan monostearate; polysorbates, such as those prepared from lauric, palmitic, stearic and oleic acids (polysorbate 20 and polysorbate 40); monononylphenyl ethers of polyethylene glycols, such as the monoxynols (e.g. octoxynol and nonoxynol); polyoxyethylene monoesters, such as polyoxyethylene monostearate, polyoxyethylene monolaurate, polyoxyethylene monoleate; dioctyl sodium sulfosuccinate; sodium lauryl sulfate, sodium laurylate, sodium laurate, polyoxyethylene-sorbitan monolaurate; and polyoxamers having a molecular weight between 2,000 and 8,000, poloxamer (182, 184, 231, 407); and mixtures thereof.

In another aspect of the present invention, additional suitable solvents for use in the present invention may include, but are not limited to, ethanol, glycerin, triethanolamine; ureas such as diazolidinyl urea; anionic, cationic, amphoteric and nonionic surfactants, including dialkyl sodium sulfosuccinate, polyoxyethylene glycerol, polyethylene glycol glyceryl stearate, polyoxyethylene stearyl ether, propoxy-ethoxybutynincopolymer, polyoxyethylene fatty alcohol ester, polyoxyethylene fatty acid ester, glycol salicylate, crotamiton, ethoxylated hydrogenated castor oil, butoxylated hydrogenated castor oil, limonene, peppermint oil, eucalyptus oil, cetyltrimethylammonium bromide, benzalkonium chloride, and Tween (20, 40, 60, 80). In one aspect of the present invention, a non-ionic surfactant may be used if the stability of oxidizable ingredients in the free form gel is affected by the ionic strength of the formulation. In one aspect of the present invention, ethanol is used as the solvent. In another aspect of the present invention, glycerin is used as the solvent. In another aspect of the present invention, the solvent or surfactant may be present in an amount from about 30 wt % to about 100% of the free form gel. The surfactant or solvent may be present in an amount up to about 30% by weight of the free form gel.

In another aspect of the present invention, the free form gel may contain up to about 10 wt % of a lipophilic or hydrophobic agent, which may serve as an emollient or anti-irritant, as an additional help in relieving irritation, if any, caused by the oxybutynin or other formulation components. Emollients suitable for use in the present invention may include lipophilic agents such as, but not limited to, fatty materials such as fatty alcohols of about 12 to 20 carbon atoms, fatty acid esters having about 12 to 20 carbon atoms in the fatty acid moiety, petrolatum, mineral oils, and plant oils such as soybean oil, sesame oil, almond oil, aloe vera gel, glycerol, and allantoin. In another aspect of the present invention glycerol is used as the emollient.

In yet another detailed aspect of the present invention, other additives may be used in order to adjust the pH of the free form gel and thus reduce irritation and/or aid in obtaining proper gelling, pH additives may be required such as, but not limited to, organic amines (e.g. methylamine, ethylamine, di/trialkylamines, alkanolamines, dialkanolamines, triethanolamine), carbonic acid, acetic acid, oxalic acid, citric acid, tartaric acid, succinic acid or phosphoric acid, sodium or potassium salts thereof, hydrochloric acid, sodium hydroxide, ammonium hydroxide and mixtures thereof.

Surprisingly, it has been discovered that in some embodiments, the specific pH of the formulation may enhance the permeation of oxybutynin through the skin as compared to another pH. As a result, in one aspect of the present invention, the oxybutynin gel formulation may have a pH that enhances oxybutynin penetration through the skin as compared to the penetration obtained at a different pH. In some aspects, the pH that aids in penetration enhancement may be a pH which is higher than a pH that does not aid in penetration enhancement. In some aspects, the pH may be a basic pH. In other aspects, the pH may be a near neutral pH. In an additional aspect, the pH may be a pH substantially equivalent to the inherent pH of the specific type of oxybutynin used. In another aspect, the specific pH may provide a permeation enhancement that is at least about 20% greater than the enhancement obtained at a different pH. Examples of specific formulations and pH therefore that enhance oxybutynin permeation are contained below.

In yet another detailed aspect of the present invention, permeation enhancers may also be added to increase the rate of permeation of the active agent, such as oxybutynin, across the epidermal layer. Useful permeation enhancers allow desired drug delivery rates to be achieved over a reasonably sized skin area, are non-toxic, cause minimal irritation, and are non-sensitizing. Although some of the solvents mentioned above also act as permeation enhancers other enhancers suitable for use in the present invention include, but are not limited to, triacetin, monoglycerides, glycerol monooleate, glycerol monolaurate, glycerol monolinoleate, glycerol dioleate, glycerol trioleate; fatty acid esters such as isopropyl myristate, isopropyl adipate, methylpropionate and ethyl oleate; thioglycerol, calcium thioglycolate, lauric acid, myristic acid, strearic acid, oleic acid, oleyl alcohol, linoleic acid, palmitic acid, valeric acid, isopropanol, isobutanol, and mixtures thereof. In one aspect of the present invention, the enhancer is a monoglyceride. In another aspect of the present invention the enhancer is triacetin.

Additional enhancers suitable for use in the present invention may include, but are not limited to, N-methylpyrrolidone, N-dodecyl pyrrolidone, hydroxypropyl-beta-cyclodextrin, lauryl alcohol, sulfoxides such as dimethylsulfoxide and decylmethylsulfoxide; ethers such as diethylene glycol monoethyl ether and diethylene glycol monomethyl ether; 1-substituted azacycloheptan-2-ones, particularly 1-n-dodecylcyclazacycloheptan-2-one (see for example, U.S. Pat. Nos. 3,989,816, 4,316,893, 4,405,616 and 4,557,934, each of which is incorporated herein by reference); alcohols such as ethanol, propanol, octanol, benzyl alcohol, and the like; amides and other nitrogenous compounds such as urea, dimethylacetamide, dimethylformamide, 2-pyrrolidone, 1-methyl-2-pyrrolidone, ethanolamine, diethanolamine and triethanolamine; terpenes; alkanones; organic acids, such as salicylic acid and salicylates, citric acid and succinic acid; certain peptides, e.g., peptides having Pro-Leu at the N-terminus and followed by a protective group (see for example, U.S. Pat. No. 5,534,496 which is incorporated herein by reference); and mixtures thereof.

In another aspect, the free form gels of the present invention may further contain about 0.05 to 2 weight % of a preservative, anti-microbial or anti-bacterial agent which prevents bacterial or microbial growth in the gel formulation. Preservatives suitable for use in the present invention may include, but are not limited to, sorbitol, p-oxybenzoic acid esters (e.g. methyl paraben, ethyl paraben, propyl paraben, etc.), benzyl alcohol, chlorobutanol, betahydroxytoluene, and thimerosal. However, other conventional preservatives commonly used in pharmaceutical compositions will be readily recognized by those skilled in the art. In one aspect of the present invention, the preservative is a paraben.

In yet another aspect of the present invention, the free form gels may include an antioxidant. Suitable antioxidants for use in the present invention may include, but are not limited to, dl-alpha-tocopherol, d-alpha-tocopherol, d-alpha-tocopherol acetate, d-alpha-tocopherol acid succinate, dl-alpha-tocopherol acid succinate, dl-alpha-tocopherol palmitate, butylated hydroxyanisole (BHA), butylated hydroxytoluene (BHT), butylatedhydroxyquinone, ethyl gallate, propyl gallate, octyl gallate, lauryl gallate, cephalm, ascorbic acid, ascorbyl oleate, ascorbyl palmitate, sodium ascorbate, calcium ascorbate, hydroxycoumarin, propylhydroxybenzoate, trihydroxybutylrophenone, dimethylphenol, ditertbutylphenol, vitamin E, lecithin and ethanolamine for example. In one aspect of the present invention, the antioxidant contains a tocopherol group. Other suitable antioxidants for oxybutynin will be readily recognized by those skilled in the art.

In still another aspect of the present invention, lubricants may be added to the free form gels of the present invention. Typical lubricants include magnesium stearate, calcium stearate, zinc stearate, magnesium oleate, magnesium palmitate, calcium palmitate, sodium suberate, potassium laurate, corn starch, potato starch, bentonite, citrus pulp, stearic acid, oleic acid, and palmitic acid.

In another aspect of the present invention, the topical formulations described herein may also be prepared with liposomes, micelles, or microspheres. Liposomes are microscopic vesicles having a lipid wall comprising a lipid bilayer. Liposomal preparations for use in the present invention include cationic, anionic and neutral preparations. Cationic liposomes suitable for use in the present invention may include, but are not limited to, N[1-2,3-dioleyloxy)propyl]-N,N,N-triethylammonium (LIPOFECTIN). Similarly, anionic and neutral liposomes may be used such as phosphatidyl choline, cholesterol, phosphatidyl ethanolamine, dioleoylphosphatidyl choline, dioleoylphosphatidyl glycerol, and dioleoylphosphatidyl ethanolamine. Methods for making liposomes using these and other materials are well known in the art.

In another detailed aspect of the present invention, micelles may be prepared to deliver oxybutynin in accordance with the method of the present invention. Micelles suitable for use in the present invention, are comprised of surfactant molecules arranged such that the polar ends form an outer spherical shell, while the hydrophobic, hydrocarbon chain ends are oriented towards the center of the sphere, forming a core. Surfactants useful for forming micelles for use in the present invention include, but are not limited to, potassium laurate, sodium octane sulfonate, sodium decane sulfonate, sodium dodecane sulfonate, sodium lauryl sulfate, docusate sodium, decyltrimethylammonium bromide, dodecyltrimethyl-ammonium bromide, tetradecyltrimethylammonium bromide, tetradecyltrimethyl-ammonium chloride, dodecylammonium chloride, polyoxyl 8 dodecyl ether, polyoxyl 12 dodecyl ether, nonoxynol 10 and nonoxynol 30. Other methods for the preparation of micelles is known to those skilled in the art.

In yet another aspect of the present invention, microspheres may also be incorporated into the present invention and encapsulate the oxybutynin and/or other components. Microspheres may be formed from lipids, such as phospholipids and preparation of microspheres generally is well known in the art.

Finally, in another aspect of the present invention, the vehicles and formulations of the present invention may optionally contain minor amounts of such other commonly used cosmetic adjuvants or other additives such as dyes, perfumes, pacifiers, sunscreens, etc., as will be readily recognized by those skilled in the art. In addition, it is also contemplated that the free form gels of the present invention may also contain other components such as vitamins, lipids, hormones, additional active agents, or anti-inflammatory agents, such as corticosteroids.

As will be appreciated by those skilled in the art, each specific type of formulation may affect the rate of delivery and present additional variables in designing the composition of such a formulation. The addition of various components may also effect the drug delivery properties of the final topical formulation. Each component of the delivery system may have independent effects or effects which occur in combination with another component and may vary depending on the particular topical formulation used.

Several of the various components listed may serve more than one purpose. Thus, although listed in one category, certain compounds may have recognized beneficial properties characteristic of another category. The above categorization is provided merely to add organization and is not meant to be a definitive classification of the compounds listed. However, these general parameters are not limitations on the way in which the desired plasma levels may be achieved. Different delivery methods, rates, and amounts may be used to affect the desired plasma levels by employing a formulation which produces different parameters.

EXAMPLES

The following examples of non-oral delivery formulations having a variety of oxybutynin containing compositions are provided to promote a more clear understanding of the possible combinations of the present invention, and are in no way meant as a limitation thereon. Materials used in the present invention were obtained from specific sources which are provided as follows. Where the materials are available from a variety of commercial sources, no specific source has been provided. Oxybutynin free base was obtained from Ceres Chemical Co. Inc., White Plains, N.Y. (USA). The enantiomers of oxybutynin and namely, the (R)- and (S)-isomers were obtained from Sepracor. Sepracor, Marlborough, Mass. (USA).

Example 1: Preparation of Oxybutynin Adhesive Matrix Patch

The non-oral oxybutynin delivery devices used in the clinical study referred to above were 13 and/or 39 cm$^2$ transdermal adhesive matrix patches. A general method of preparing transdermal adhesive matrix patches is described by U.S. Pat. Nos. 5,227,169, and 5,212,199, which are incorporated by reference in their entirety. Following this general method, the oxybutynin patches of this invention were prepared as follows:

Oxybutynin free base, triacetin (Eastman Chemical Co., Kingsport, N.Y.) and 87-2888 acrylic copolymer adhesives (National Starch and Chemical Co., Bridgewater, N.J.) were mixed into a homogenous solution and coated at 6 mg/cm$^2$ (dried weight) onto a silicone treated polyester release liner (Rexam Release, Chicago, Ill.) using a two zone coating/drying/laminating oven (Kraemer Koating, Lakewood, N.J.) to provide a final oxybutynin adhesive matrix containing 15.4%, 9.0%, and 75.6% by weight oxybutynin, triacetin and acrylic copolymer adhesive, respectively. A fifty micron thick polyethylene backing film (3M, St. Paul, Minn.) was subsequently laminated onto the dried adhesive surface of the oxybutynin containing adhesive matrix and the final laminate structure was die cut to provide patches ranging in size from 13 cm$^2$ to 39 cm$^2$ patches.

Example 2: Preparation of Oxybutynin Biodegradable Microsphere Depot Injection

Biodegradable microspheres for effecting a sustained-release depot injection may be used to deliver oxybutynin in accordance with the method of the present invention. Microspheres were prepared by the following method:

12,000 molecular weight poly-d,l lactic acid ("PLA", Birmingham Polymers, Birmingham, Ala.) was dissolved into methylene chloride at a final concentration of 20% by weight. Oxybutynin free base was dissolved into the PLA solution at 4% by weight in the final solution. A water-jacketed reaction vessel (temperature controlled at 5 degrees Celsius) equipped with a true-bore stirrer fitted with a Teflon turbine impeller was charged with a de-ionized water containing 0.1% Tween 80.

The oxybutynin/PLA/methylene chloride solution was added drop wise into the reaction vessel and stirred to dispense the organic polymer phase within the aqueous solution as fine particles. The resultant suspension was filtered and washed once with de-ionized water and finally dried on a rotary evaporator to removed methylene chloride. The resultant microspheres can be injected either intramuscularly or subcutaneously to provide a prolonged systemic release of oxybutynin.

Example 3: Preparation of Topical Oxybutynin Formulation

Topically applied oxybutynin containing gel may be used to deliver oxybutynin in accordance with the method of the present invention. A general method of preparing a topical gel is known in the art. Following this general method, a topical gel comprising oxybutynin was prepared as follows:

95% ethanol (USP) was diluted with water (USP), glycerin (USP), and glycerol monooleate (Eastman Chemical, Kingsport N.Y.) to provide a final solution at ethanol/water/glycerin/glycerol monooleate percent ratios of 35/59/5/1, respectively. Oxybutynin free base was then dissolved into the above solution to a concentration of 10 mg/gram. The resultant solution was then gelled with 1% hydroxypropyl cellulose (Aqualon, Wilmington, Del.) to provide a final oxybutynin gel. One to two grams of the above gel is applied topically to approximately 200 cm$^2$ surface area on the chest, torso, and/or arms to provide topical administration of oxybutynin.

Example 4: Clinical Study to the Determine the Pharmacokinetics of Oxybutynin, N-Desethyloxybutynin, and their Respective (R) and (S) Isomers Following Oral Administration of Racemic Oxybutynin in Comparison to Transdermally Administered Racemic Oxybutynin A clinical study in 16 healthy volunteers compared, in a cross-over fashion, the comparative plasma concentrations and pharmacokinetics of oxybutynin, N-desethyloxybutynin, and their respective (R)- and (S)-enantiomeric components.

Healthy volunteers were recruited from the local population and included men and women ranging in age from 19 to 45 years. Following a pre-study examination to confirm a healthy condition in all volunteers, each subject participated in 2 study periods during which the test medications, either a transdermal oxybutynin system applied for 4 days or a single 5 mg oral immediate-release dose of oxybutynin, were administered. Blood samples were collected periodically throughout the study periods. Plasma was harvested from the samples according to a standard method. The quantities of (R) and (S) oxybutynin and (R) and (S) N-desethyloxybutynin were measured in the plasma samples through the application of a validated mass spectrometric method coupled with liquid chromatographic separation of the individual constituents. A Perkin Elmer high performance liquid chromatographic pump was used in conjunction with a Chrom Tech AGP 150.2 chromatographic column. The mass spectrometry instrument was an API 300 operated in MRM scan mode with electrospray ionization. A linear response of the quantitation of the analytes was confirmed with standard solutions and the performance of the assay was controlled using quality control samples analyzed in conjunction with the study samples. The range of linearity was 0.5 to 75 ng/ml with linear correlation coefficients greater than 0.99 for all analytes.

FIGS. 1, 2, 3, 6, and 7 show graphical displays of these data. In FIG. 1, oxybutynin and N-desethyloxybutynin plasma concentrations are shown following administration of the 5 mg immediate-release oral dosage oxybutynin hydrochloride tablets, Ditropan® Alza Corporation. These tablets were obtained commercially and can be obtained from various generic manufacturers. Plasma concentration is indicated on the vertical axis, and time is indicated on the horizontal axis. As can be seen, the plasma concentrations of N-desethyloxybutynin are significantly greater than oxybutynin plasma concentrations. The mean AUC ratio for N-desethyloxybutynin to oxybutynin is about 10:1.

Figure 3:
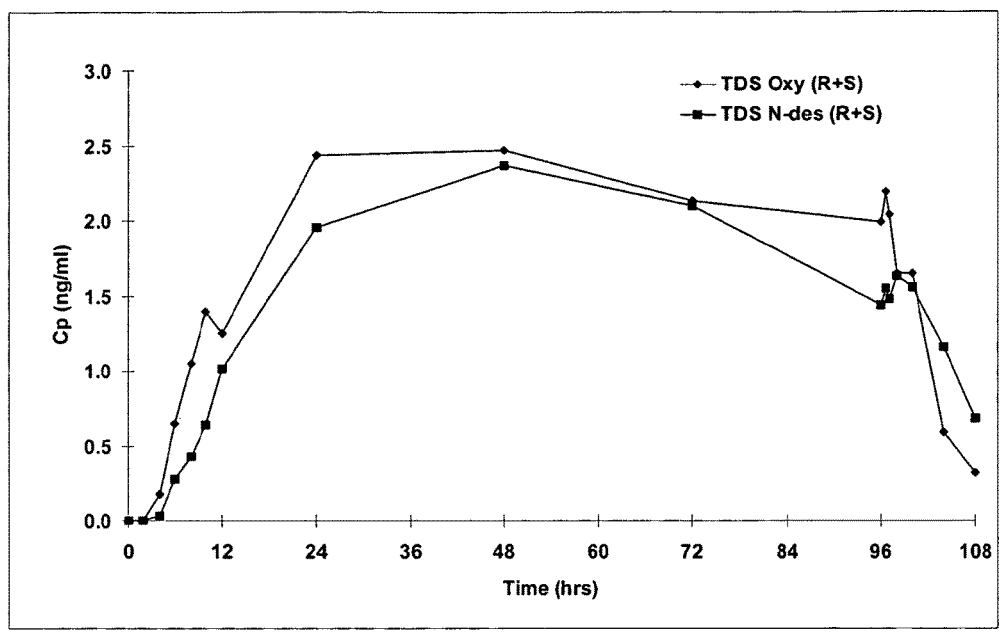
FIG. 3 is a graphical representation of total oxybutynin and N-desethyloxybutynin plasma concentrations measured upon transdermal administration according to the present invention, spanning a time from initial oxybutynin administration to 96 hours therefrom, and for an additional 12 hours following the removal of the transdermal system at 96 hours.

FIG. 3 illustrates the plasma concentration profiles for oxybutynin and N-desethyloxybutynin during and following application of the transdermal system. As can be seen, the N-desethyloxybutynin plasma concentrations for the adhesive matrix patch embodiment, fall well within the parameters prescribed by the present invention. The mean AUC ratio for N-desethyloxybutynin to oxybutynin is about 0.9:1 and the mean plasma concentrations for N-desethyloxybutynin are less than about 2.5 ng/ml.

FIGS. 6 and 7 illustrate the plasma concentrations of the individual isomers of oxybutynin and N-desethyloxybutynin as measured during the clinical trial described above. As can be seen in FIG. 6, oral administration of oxybutynin leads to relatively high concentrations of (R)—N-desethyloxybutynin. This active metabolite moiety is present in the greatest concentration, and is several times the concentration of both (R) and (S) oxybutynin. The mean ratio of AUC of (R)—N-desethyloxybutynin to (R)-oxybutynin is about 17:1 and the mean AUC ratio of (R)—N-desethyloxybutynin to (S)—N-desethyloxybutynin is about 1.5:1.

Following application of the transdermal oxybutynin system, the mean AUC ratio of the active moieties, (R)—N-desethyloxybutynin to (R)-oxybutynin, is about 1:1, substantially lower than following oral administration. Additionally, the mean AUC ratio of (R)—N-desethyloxybutynin to (S)—N-desethyloxybutynin is about 0.9:1, consistent with substantially lower metabolic first pass conversion of the active (R)-oxybutynin to (R)—N-desethyloxybutynin. The mean AUC ratio of (R)- to (S)-oxybutynin is about 0.7:1, similar to that present following oral administration.

The lower overall amount of oxybutynin delivered during transdermal delivery of oxybutynin was estimated based on the residual amount of oxybutynin remaining in the transdermal system after the 4-day application period subtracted from the amount determined in unused transdermal systems. The mean amount delivered over 4 days was about 12 mg or an average of about 3 mg/day. The oral dose of oxybutynin administered in the study was 5 mg, a dose that may be administered every 12 hours, or two times daily, during therapeutic use of the product. This allows a comparison of a dose of about 5 mg every 12 hours for oral treatment compared to about 1.5 mg every 12 hours for transdermal treatment.

In summary, the pharmacokinetics of transdermal, non-oral, oxybutynin administration illustrate the aspects of the invention with regard to a sustained, slower rate of administration of oxybutynin and a lower dose or overall amount of oxybutynin administered.

Example 5: Comparative Analysis of Therapeutic Efficacy and Incidence and Severity of Anticholinergic Side Effects, Primarily Dry Mouth of Conventional Oral Tablet Formulation and Transdermal Formulation of the Present Invention A clinical study of the efficacy and incidence of side effects was conducted in 72 patients with overactive bladder. These patients were recruited by independent clinical investigators located in various regions of the U.S.A. Approximately half of the patients were administered oxybutynin hydrochloride in an immediate-release oral dosage formulation. The remaining patients were administered oxybutynin using in each case one or more 13 $cm^2$ oxybutynin containing transdermal adhesive matrix patches. In each of these treatment groups, the medications were blinded by the concomitant administration of matching placebo forms of the treatments. In the case of active oral treatment, the patients applied placebo transdermal systems that contained all ingredients of the active transdermal system with the exception of the active drug oxybutynin. In like fashion, the active transdermal treatment group received matching oral formulations without the active oxybutynin constituent.

In this study, the patients included both men and women, with the majority being women with an average age of 63-64 years. All patients had a history of urinary incontinence associated with overactive bladder and demonstrated a mean of at least 3 incontinent episodes per day during a washout period during which no medical therapy for incontinence was used.

Therapeutic efficacy was based on the mean number of incontinent episodes experienced per day as derived from a multiple-day patient urinary diary. The data are displayed graphically in FIG. 4.

As can be seen, the number of incontinent episodes for those individuals treated by the non-oral method of the present invention is nearly identical to the number for those treated with the oral formulation. This indicates clearly that the present methods and compositions provide for a therapeutically effective treatment for urinary incontinence and overactive bladder that is comparable to the conventional oral formulation, such as a 5 mg oral oxybutynin tablet. Incidence and/or severity of adverse drug experience was also compared between the conventional oral tablet formulation of oxybutynin administered as above and the transdermal formulation. Anticholinergic adverse experience, such as the incidence and severity of dry mouth, was used as an indicator of the adverse experience that can be associated with the administration of either formulation and represents an anticholinergic side effect. The clinical study participants were asked to report this experience according to a standardized questionnaire. The data derived from the questionnaire are displayed graphically in FIG. 5. The percentage of participants reporting dry mouth is indicated on the vertical axis, and the severity of the dry mouth is indicated on the horizontal axis.

As can be seen, only 6% of the participants who received the oral form reported no dry mouth effects. Conversely, 94% of these participants reported experiencing some dry mouth. By contrast, 62% of the participants who were treated with the 13 cm² transdermal adhesive matrix patches reported no dry mouth effects. Therefore, only 38% of these participants reported experiencing some dry mouth. Therefore, the clinical data shows that matrix patch embodiment of the method of the present invention, provides a treatment for overactive bladder which achieves nearly identical therapeutic effectiveness as an oral form, while significantly minimizing the incidence and/or severity of adverse experiences associated with oxybutynin administration.

FIG. 7 shows that the (R)—N-desethyloxybutynin concentrations are lower than the (S)—N-desethyloxybutynin concentrations, and further, the concentrations of (R)-oxybutynin increase slowly and are maintained at an approximately constant level throughout the patch application time period. The reduced plasma concentrations of (R)—N-desethyloxybutynin appears to have contributed to the minimization of the incidence and severity of adverse drug experiences such as dry mouth, while the plasma concentrations of (R)-oxybutynin retain the therapeutic effectiveness of the treatment, as shown by FIGS. 4 and 5.

Example 6: Preparation of Free Form Oxybutynin Gel

A topically applied oxybutynin containing gel may be used to deliver oxybutynin in accordance with the method of the present invention. The gel of the present invention, and those described in Examples 9 through 11, were made by weighing glycerin (or other humectants and emollients) into a 6 oz jar, then pre-weighed water was added, followed by pre-weighed 2N sodium hydroxide (for oxybutynin chloride gel) or 2N hydrochloride (for oxybutynin free base gel). The sodium hydroxide or sodium hydrochloride may be present at from 0 wt % to about 5 wt % of the total free form gel. Pre-weighed ethanol was added into a 6 oz jar. The active ingredient (either oxybutynin free base or oxybutynin chloride) was weighed into a weighing dish on an analytical balance then transferred into the 6 oz jar. After being tightly capped, the jar was hand shaken until both the active ingredient and glycerin completely dissolved. Next, pre-weighed gelling agent was transferred into the jar (agglomeration of the gelling agent can be avoided by slow dispersion of the gelling agent particles into the jar). The actual weights of each ingredient was determined by the difference in the transfer container weight. The jar was capped, wrapped with parafilm and put on a wrist shaker overnight to completely dissolve the gelling agent.

Example 7: Experimental Methods and In Vitro Flux Study for Free Form Oxybutynin Gel In vitro skin flux studies of Examples 9 through 11 were conducted using full-thickness skin samples (approximately 500 μm) obtained from skin banks. The full-thickness skin samples were stored at −5° C. until experiments were conducted. The gender, age, sex and anatomical site information for each donor was recorded when available.

The method used to apply a thin film of gel to the surface of the skin was adapted from Chia-Ming Chiang et al., *Bioavailability assessment of topical delivery systems: in vitro delivery of minoxidil from prototypical semi-solid formulations*, IJP, 49:109-114, 1989, which is incorporated herein by reference. The stratum corneum side of a piece of skin was attached to one side of an adhesive-coated metal shim having a circular hole of 0.64 cm² cut in the center. The shim-membrane assembly was placed on top of a flat glass surface, and approximately 15 μL of a formulation was dispensed into the central cavity. With a microscope slide, the gel was spread across the surface of the skin, loading a dose of approximately 7 μL over the 0.64 cm² diffusional surface area. The applied dose was approximately 11 μL of gel per cm² diffusional surface area, which is typical for topical applications.

The gel-loaded shim-membrane assembly was clamped between the donor and receiver compartments of a modified Franz diffusion cell with the dermal side facing the receiver solution. The receiver compartment was filled with 0.02% (w/v) $NaN_3$ to maintain sink conditions on the receiver side throughout the duration of the experiment. The donor compartment was unoccluded and open to the atmosphere. Cells were placed in a water bath heated with circulating water and calibrated to maintain the skin surface temperature at $(32\pm1)°$ C.

At predetermined time points, the entire contents of the receiver compartment was collected for quantifying the amount of drug, and the receiver compartment refilled with fresh receptor medium, taking care to eliminate any air bubbles at the skin/solution interface. Each of the samples were analyzed using high performance liquid chromatography (HPLC). The cumulative amount of drug permeated per unit area at any time t ($Q_t$, μg/cm²) was determined over a 24-hr period as follows:

$$Qt = \sum_{n=0}^{t} \frac{C_n V}{A}$$

where, $C_n$ is the concentration (μg/mL) of the drug in the receiver sample at the corresponding sample time, V is the volume of fluid in the receiver chamber, and A is the diffusional area of the cell (0.64 cm²).

For the studies of Examples 8 through 10, typically four replicates were obtained per skin per system. A comparison of the means of the values obtained for a given system from each skin indicated differences in permeation due to differences in skin.

Example 8: Topical Oxybutynin Free Base Gel

Example 8.1

TABLE 1

| Formulation[a] Et/E/G/D (% w/w) | $Q_t$ (t = 24 hours) (μg/cm²/t)[b] | $J_{ss}$ (μg/cm²/t)[b] |
|---|---|---|
| 84.5/10/1.5/4 | 29.20 ± 20.24 | 1.22 ± 0.84 |
| 80.5/10/1.5/8 | 44.92 ± 18.12 | 1.87 ± 0.76 |

[a]Et = ethanol; E = enhancer = triacetin; G = gelling agent = KLUCEL; D = drug = oxybutynin free base
[b]Mean ± SD (n = 4 skin donors)

These results show that an increase in permeation rate may be achieved by increasing the concentration of oxybutynin in the formulation. Thus, in one aspect of the invention, a method of increasing the oxybutynin flux rate by increasing the concentration of oxybutynin in the formulation is provided.

Example 8.2

TABLE 2

| Formulation[a] Et/W/G/D (% w/w) | $Q_t$ (t = 24 hours) (μg/cm$^2$/t)[b] | $J_{ss}$ (μg/cm$^2$/t)[b] |
|---|---|---|
| 94.5/0/1.5/4.0 | 14.04 ± 9.47 | 0.56 ± 0.39 |
| 74.5/20/1.5/4.0 | 19.11 ± 17.40 | 0.80 ± 0.73 |

[a]Et = ethanol; W = water; G = gelling agent = KLUCEL; D = drug = oxybutynin free base
[b]Mean ± SD (n = 4 skin donors)

These results show that acceptable flux rates can be achieved using both aqueous and non-aqueous gel formulations. The results further show that flux rates may be increased by using an aqueous formulation. Thus, a method is provided for increasing the flux rate of an oxybutynin by increasing the water concentration contained in an oxybutynin gel formulation. In one aspect, the amount of water can be increased by about 1% w/w to about 30% w/w. In another aspect, the amount of water can be increased by about 5% w/w to about 25% w/w. In yet another aspect, the amount of water can be increased by about 10% w/w to about 20% w/w. In one detailed aspect, the oxybutynin in the formulation maybe an oxybutynin free base.

Example 8.3

TABLE 3

| Enhancer | Formulation[a] Et/E/G/D (% w/w) | $Q_t$ (t = 24 hours) (μg/cm$^2$/t)[b] | $J_{ss}$ (μg/cm$^2$/t)[b] |
|---|---|---|---|
| None | 94.5/0/1.5/4.0 | 10.02 ± 5.38 | 0.42 ± 0.22 |
| Triacetin | 84.5/10.0/1.5/4.0 | 14.73 ± 6.70 | 0.61 ± 0.28 |

[a]Et = ethanol; E = enhancer; W = water; G = gelling agent = KLUCEL; D = drug = oxybutynin free base
[b]Mean ± SD (n = 4 skin donors)

Example 8.4

TABLE 4

| pH of gel | Formulation[a] Et/W/G/D (% w/w) | $Q_t$ (t = 24 hours) (μg/cm$^2$/t)[b] | $J_{ss}$ (μg/cm$^2$/t)[b] |
|---|---|---|---|
| 6.0 | 74.5/20.0/1.5/4.0 | 15.90 ± 4.16 | 0.66 ± 0.17 |
| 9.8 | 74.5/20.0/1.5/4.0 | 20.71 ± 3.42 | 0.86 ± 0.41 |

[a]Et = ethanol; W = water; G = gelling agent = KLUCEL; D = drug = oxybutynin free base
[b]Mean ± SD (n = 4 skin donors)

Thus, a method is provided for increasing oxybutynin flux rate by increasing the pH of the formulation. In one aspect, the formulation is a gel formulation and the pH is increased from about 4 to about 11. In another aspect, the pH is increased from about 5 to about 11. In yet another aspect, the pH is increased from about 6 to about 11. In another aspect, the pH is increased from about 4 to about 10. In yet another aspect, the pH is increased from about 5 to about 10. In another aspect, the pH is increased from about 6 to about 10. In yet another aspect, the pH is increased from about 6 to about 9. In one aspect, the pH of the gel formulation is about 6. In yet another aspect, the pH of the gel formulation is about 9. It should be understood that the oxybutynin is present in either as its free base form, or its pharmaceutically acceptable salt (e.g., HCl) or a mixture thereof. In another aspect, the oxybutynin may be present as its R- or its S-isomer or its pharmaceutically acceptable salt or a mixture thereof. Moreover, the formulation may be prepared with or without a permeation enhancer. Thus, in one aspect, a method of increasing the oxybutynin flux rate from a topical formulation of oxybutynin by increasing the pH of the formulation which is substantially free of a permeation enhancer. In another aspect, a method of increasing the oxybutynin flux rate from a topical formulation of oxybutynin by increasing the pH of the formulation which may include a permeation enhancer. When the formulation comprises a permeation enhancer, the formulation may provide an increased flux rate compared to a formulation that comprises an increased pH but substantially free of an enhancer. In some aspects, the flux rate may be increased by at least two-fold. In some other aspects, the flux rates may be increased by 2-3 times, or even higher. In yet some other aspects, the flux rate may be increased by 5-10 fold. It should also be understood that the increased flux rates due to increased pH could be achieved with other topical formulations, such as creams, ointments, lotions, foams, sprays, and transdermal patches, and not necessarily limited to the gel formulations.

Example 8.5

TABLE 5

| Formulation[a] Et/W/Gl/G/D (% w/w) | $Q_t$ (t = 24 hours) (μg/cm$^2$/t)[b] | $J_{ss}$ (μg/cm$^2$/t)[b] |
|---|---|---|
| 74.0/20.0/0/2.0/4.0 | 13.26 ± 10.89 | 0.55 ± 0.45 |
| 74.0/19.0/1.0/2.0/4.0 | 11.68 ± 10.63 | 0.49 ± 0.44 |

[a]Et = ethanol; W = water; Gl = glycerin; G = gelling agent = KLUCEL; D = drug = oxybutynin free base
[b]Mean ± SD (n = 4 skin donors)

These results show that the incorporation of glycerin into the gel has no measurable impact on the skin permeation of oxybutynin. Therefore, glycerin can be used in a topical oxybutynin gel formulation in order to reduce skin irritation, or for other reasons as will be recognized by one of ordinary skill in the art.

Example 9: Oxybutynin and N-Desethyloxybutynin Plasma Concentrations after a Single Application of a 4.4% Oxybutynin Topical Gel Formulation to the Abdomen of Healthy Subjects A clinical study in 22 healthy volunteers, 19 to 45 years of age, evaluated plasma concentrations of oxybutynin and the N-desethyloxybutynin metabolite after a single topical application of oxybutynin gel. The study employed a single dose design to evaluate the pharmacokinetics and skin tolerability of a gel formulation for oxybutynin hydrochloride.

Volunteers received a single topical administration of 3 g of 4.4% oxybutynin gel to a 400 cm$^2$ area of unbroken skin on the abdomen. Blood samples were periodically collected throughout the study period and plasma was harvested according to standard procedures. Plasma oxybutynin and N-desethyloxybutynin metabolite concentrations were estimated using a high performance liquid chromatography-tandem mass spectrometry method performed according to established guidelines.

Figure 8:
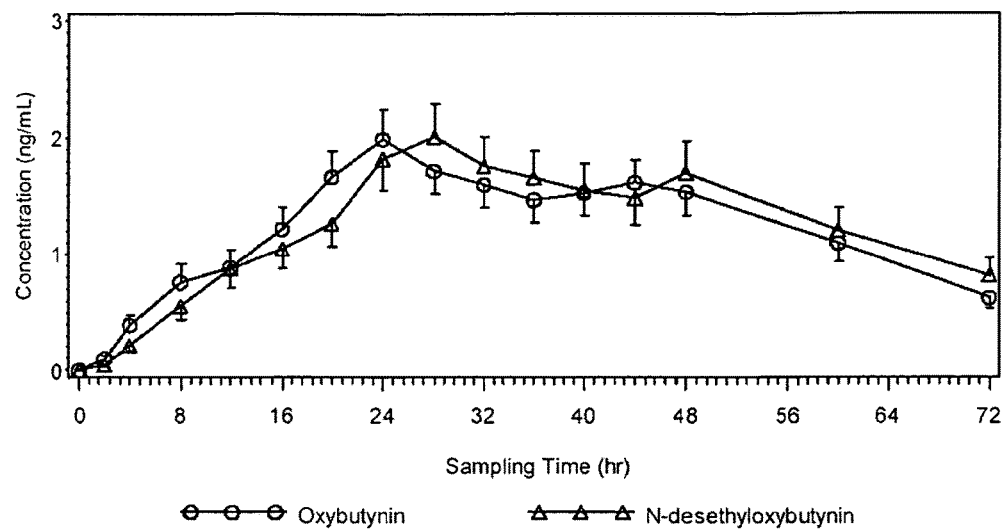
FIG. 8 is a graphical representation of the plasma concentrations of oxybutynin and N-desethyloxybutynin following topical application of 4.4% oxybutynin gel in accordance with the present invention.

FIG. 8 shows oxybutynin and N-desethyloxybutynin plasma concentrations during the study period. Plasma concentration is indicated on the vertical axis, and time is indicated on the horizontal axis. After application of the oxybutynin gel, measurable levels of oxybutynin were detectable in plasma at the first sampling point (2 hours) following dosing. Mean plasma oxybutynin levels increased steadily during the following 24 hours to a maximum plasma concentration ($C_{max}$) of 2.17 ng/mL. Thereafter plasma drug concentrations decreased with an elimination half-life of approximately 18.45 hours. A second peak approximately 48 hours after dosing was also apparent.

Measurable levels of N-desethyloxybutynin were detectable in plasma at the first sampling point (2 hours) following dosing. Mean plasma N-desethyloxybutynin levels increased steadily during the following 28 hours to a $C_{max}$ of 2.20 ng/mL. Thereafter plasma concentrations decreased with an elimination half-life of approximately 26.81 hours. Again, a second peak approximately 48 hours after dosing was also apparent. The mean AUC ratio for oxybutynin:N-desethyloxybutynin was about 0.98:1.

Example 10: Oxybutynin and N-Desethyloxybutynin Plasma Concentrations after a Single Application of a 13.2% Oxybutynin Topical Gel Formulation to the Abdomen of Healthy Subjects A clinical study in 22 healthy volunteers, 19 to 45 years of age, evaluated plasma concentrations of oxybutynin and the N-desethyloxybutynin metabolite after a single topical application of oxybutynin gel. The study employed a single dose design to evaluate the pharmacokinetics and skin tolerability of a gel formulation for oxybutynin hydrochloride.

Volunteers received a single topical administration of 1 g of 13.2% oxybutynin gel to a 133 cm² area of unbroken skin on the abdomen. Blood samples were periodically collected throughout the study period and plasma was harvested according to standard procedures. Plasma oxybutynin and N-desethyloxybutynin metabolite concentrations were estimated using a high performance liquid chromatography-tandem mass spectrometry method performed according to established guidelines.

Figure 9:
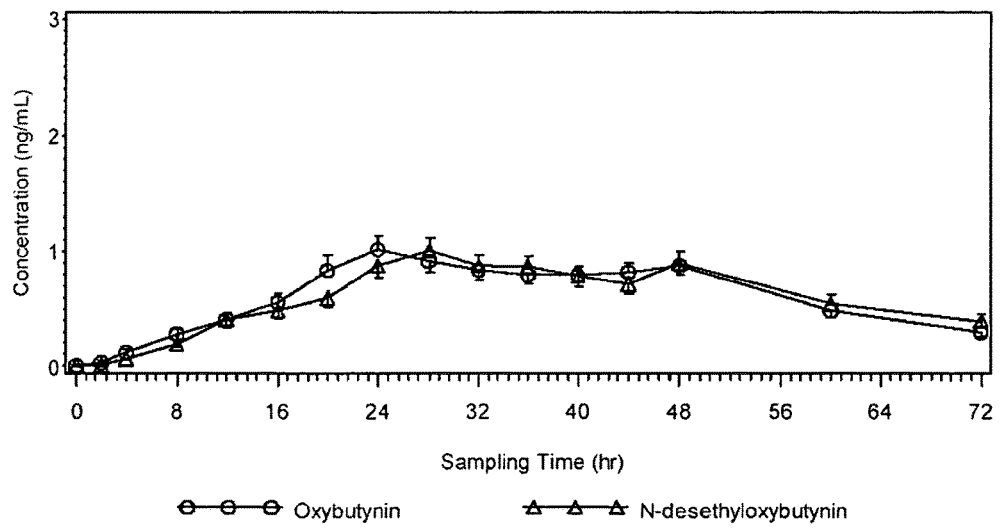
FIG. 9 is a graphical representation of the plasma concentrations of oxybutynin and N-desethyloxybutynin following topical application of 13.2% oxybutynin gel in accordance with the present invention.

FIG. 9 shows oxybutynin and N-desethyloxybutynin plasma concentrations during the study period. Plasma concentration is indicated on the vertical axis, and time is indicated on the horizontal axis. After application of the 13.2% gel, measurable levels of oxybutynin were detectable in plasma at the first sampling point (2 hours) following dosing. Mean plasma oxybutynin levels increased steadily during the following 26 hours to a Cmax of 1.17 ng/mL. Thereafter plasma drug concentrations decreased with an elimination half-life of 17.71 hours. As observed with the 4.4% gel formulation in Example 9, a second peak approximately 48 hours after dosing was also apparent.

Measurable levels of N-desethyloxybutynin were detectable in plasma at the first sampling point (2 hours) following dosing. Mean plasma N-desethyloxybutynin levels increased steadily during the following 28 hours to a $C_{max}$ of 1.12 ng/mL. Thereafter plasma concentrations decreased with an elimination half-life of 19.53 hours. Again, a second peak approximately 48 hours after dosing was apparent. The mean AUC ratio for oxybutynin:N-desethyloxybutynin was about 1:0.99.

Example 11: Oxybutynin and N-Desethyloxybutynin Plasma Concentrations after Single and Repeated Application of an Oxybutynin Topical Gel Formulation to the Abdomen of Healthy Subjects A clinical study in 12 healthy volunteers, 19 to 41 years of age, evaluated plasma concentrations of oxybutynin and the N-desethyloxybutynin metabolite after single and repeated topical applications of oxybutynin gel. The study employed a single-period, open-label, multiple dose design to evaluate the pharmacokinetics and skin tolerability of a gel formulation for oxybutynin hydrochloride.

Volunteers received topical administrations of 3 g of 4.4% oxybutynin gel on 3 consecutive mornings. Each volunteer received the oxybutynin gel administrations on a defined area of unbroken skin on the abdomen. Blood samples were periodically collected throughout the study period and plasma was harvested according to standard procedures. Plasma oxybutynin and N-desethyloxybutynin metabolite concentrations were estimated using high performance liquid chromatography-tandem mass spectrometry method performed according to established guidelines.

Figure 10:
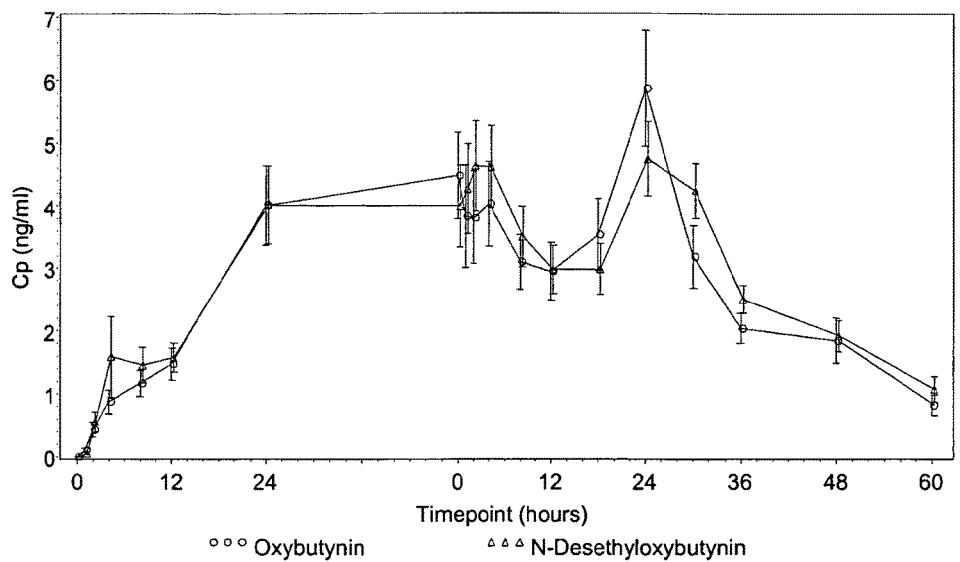
FIG. 10 is a graphical representation of the plasma concentrations of oxybutynin and N-desethyloxybutynin following single and repeated topical application of 4.4% oxybutynin gel in accordance with the present invention.

FIG. 10 shows oxybutynin and N-desethyloxybutynin plasma concentrations for the duration of the study period. Plasma concentration is indicated on the vertical axis, and time is indicated on the horizontal axis. After the initial gel application, low levels of oxybutynin appeared in plasma within one hour following dosing. Mean plasma oxybutynin levels increased steadily during the following 24 hours to a mean±SD concentration of 4.02±2.19 ng/mL at the 24 hour post-dose timepoint. Drug levels measured 24 hours after the second application (4.47±2.38 ng/mL) were similar to the initial 24 hour post-dosing levels, but considerably higher at the 24 hour post-dose timepoint following the third application (5.86±3.17 ng/mL). $C_{max}$ occurred 24 hours following gel application in both assessment periods and was 6.05±3.21 ng/mL following the third application.

A complete characterization of the dosing interval following the third application showed a drop in oxybutynin concentration for the first 12 hours following gel application and then rising again to maximum levels at the 24 hour timepoint. Plasma oxybutynin decreased steadily for 36 hours following the 24 hour timepoint but did not reach baseline during the sampling period. This elimination was consistent with an apparent half-life of approximately 18 hours, presumably due to a skin depot effect.

N-desethyloxybutynin kinetics followed a similar pattern as oxybutynin throughout the study period. However, there appears to be a potential diurnal or possibly postural variation in the relationship between N-desethyloxybutynin and the parent compound. Initially, N-desethyloxybutynin levels were consistently higher than those of the parent compound following gel application through the 12 hour time point from both applications 1 and 3. However, at subsequent time points during the next 12 hours in both evaluation periods, oxybutynin levels exceeded N-desethyloxybutynin levels. Thereafter, at each evaluation during the elimination phase, N-desethyloxybutynin levels were higher than oxybutynin. The mean AUC ratio for oxybutynin:N-desethyloxybutynin was 1:0.98.

Example 12: An Evaluation of the Single and Multiple Dose Pharmacokinetics of Oxybutynin and N-Desethyloxybutynin Following Administration of Oxybutynin Gel in Healthy Volunteers A clinical study in 20 healthy volunteers, 20 to 44 years of age, evaluated the single and multiple dose pharmacokinetics of oxybutynin and N-desethyloxybutynin following topical oxybutynin gel administration. The study employed a two-period multiple dose study.

In the first treatment period, volunteers received a topical administration of 3 g of 4.4% oxybutynin gel followed by a 72 hour evaluation period. The second treatment period, oxybutynin gel was administered topically to the volunteers on 7 consecutive mornings. The two treatment periods were separated by a 7-day washout period. Blood samples were periodically collected throughout the study periods and plasma was harvested according to standard procedures. Plasma oxybutynin and N-desethyloxybutynin metabolite concentrations were estimated using high performance liquid chromatography-tandem mass spectrometry method performed according to established guidelines.

Figure 11:
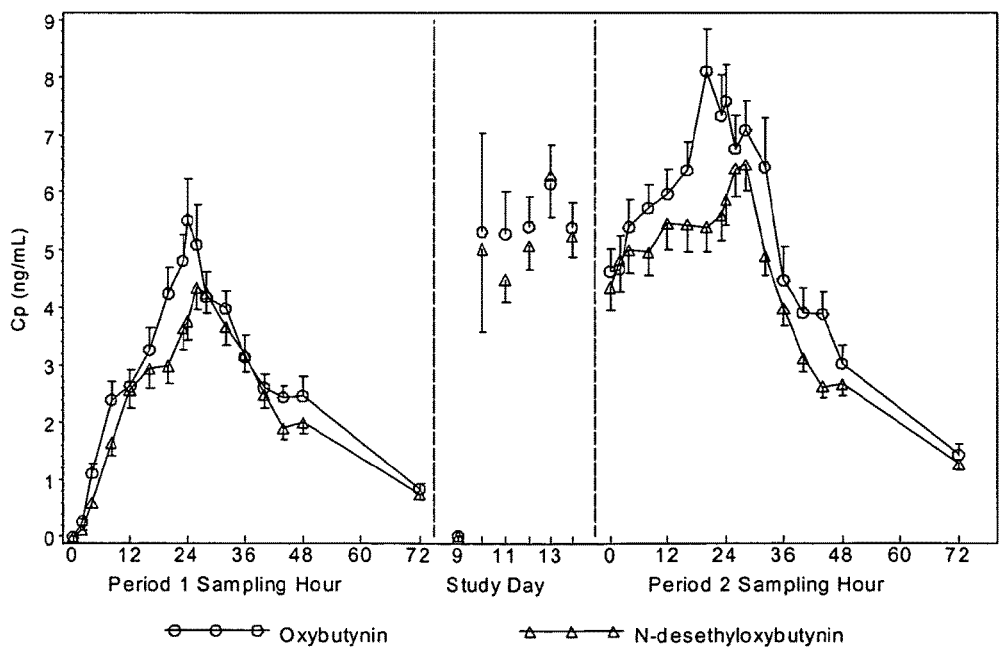
FIG. 11 is a graphical representation of the plasma concentrations of oxybutynin and N-desethyloxybutynin following single and repeated topical application of 4.4% oxybutynin gel in accordance with the present invention.

FIG. 11 shows oxybutynin and N-desethyloxybutynin plasma concentrations for the duration of the study period. After the initial 3 g oxybutynin gel application, measurable levels of oxybutynin were detectable in plasma within two hours following dosing. Mean plasma oxybutynin levels increased steadily during the following 24 hours to a $C_{max}$ of 6.35 ng/mL. Thereafter plasma drug concentrations decreased in an apparent biphasic manner with an elimination half-life of approximately 18 hours. Mean plasma N-desethyloxybutynin concentrations followed a similar pattern as the parent compound with a slight lag time, reaching $C_{max}$ (4.50 ng/mL) approximately 26 hours following gel application.

Mean oxybutynin $C_{max}$ and AUC (186 ng·hr/mL) were approximately 18% and 41% higher, respectively, than the mean N-desethyloxybutynin $C_{max}$ and AUC (157 ng·hr/mL). The mean (SD) oxybutynin:N-desethyloxybutynin AUC ratio for the 72 hour treatment period was 1:0.87.

After a 7-day washout following the initial gel application, subjects applied daily 3 g doses of oxybutynin gel to rotating body sites (abdomen, upper arms, thighs) for 7 consecutive days. Plasma samples were drawn each morning before the next gel application.

Daily morning mean (SD) plasma concentrations were similar following the outpatient gel applications on Days 10-15, ranging from 4.63 ng/mL to 6.15 ng/mL. Following the final gel application, mean plasma oxybutynin concentrations rose above Time 0 levels (4.63 ng/mL) to a $C_{max}$ of 9.01 ng/mL approximately 23 hours after gel application. Mean drug concentrations decreased during the following 48 hours with an elimination half-life of approximately 24 hours. The average (SD) plasma concentration during the 20 hours following the application was 6.22 ng/mL.

Mean plasma N-desethyloxybutynin concentrations increased in a more gradual manner and to a lesser extent than the parent compound, reaching maximum concentration (6.44 ng/mL) for the 0-24 hour interval at approximately 16 hours. Higher levels were attained following the 24 hour timepoint.

Mean oxybutynin $C_{max}$ and AUC (149 ng·hr/mL) were approximately 40% and 19% higher, respectively, than the mean N-desethyloxybutynin $C_{max}$ and AUC (125 ng·hr/mL). The mean (SD) oxybutynin:N-desethyloxybutynin AUC ratio for the first 24 hours of the treatment period was 1:0.87.

Example 13: Single-Dose Pharmacokinetics of Oxybutynin and N-Desethyloxybutynin Following the Application of Topical Oxybutynin Gel to 400 $cm^2$ and 800 $cm^2$ Application Areas on the Thighs of Healthy Volunteers A clinical study in 21 healthy volunteers, 21 to 45 years of age, evaluated the effect of application surface area on the single-dose pharmacokinetic of oxybutynin following topical oxybutynin gel administration. The study employed a two-period, open-labeled, randomized crossover design to evaluate the effect of application surface area on the single dose pharmacokinetics and safety of a topical gel formulation of oxybutynin hydrochloride.

Volunteers received topical administrations of 3 g of 4.4% oxybutynin gel at the beginning of two 72 hour treatment periods, with a minimum six day washout separating the treatment periods. Each volunteer received a dose applied to a 400 $cm^2$ area in one treatment period, and a dose to an 800 $cm^2$ area the other treatment period. The sequential order of the treatment periods was randomized. Blood samples were periodically collected throughout the study periods and plasma was harvested according to standard procedures. Plasma oxybutynin and N-desethyloxybutynin metabolite concentrations were evaluated using high performance liquid chromatography-tandem mass spectrometry method performed according to established guidelines.

Figure 12:
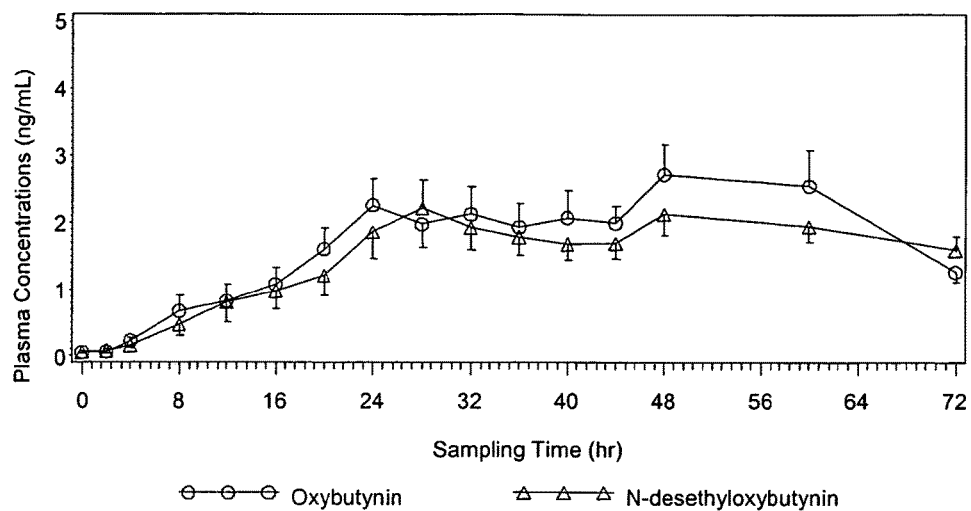
FIG. 12 is a graphical representation of the plasma concentrations of oxybutynin and N-desethyloxybutynin following topical application of 4.4% oxybutynin gel to a 400 cm² patch[AREA?] of skin in accordance with the present invention.

FIG. 12 shows oxybutynin and N-desethyloxybutynin plasma concentrations following oxybutynin gel application to a 400 $cm^2$ application area for the duration of the study period. After gel application to the 400 $cm^2$ application area, measurable levels of oxybutynin were detectable in plasma at the first sampling timepoint following dosing (2 hours). Mean plasma oxybutynin levels increased steadily to a peak at the 24 hour timepoint of 2.25 ng/mL. This initial peak was followed by diminishing levels for approximately 12 hours, followed by a second peak ($C_{max}$) of 3.70 ng/dL at 48 hours post-dose. Thereafter plasma drug concentrations gradually decreased toward baseline during the following 24 hours.

N-desethyloxybutynin levels essentially mimicked those of the parent compound, with measurable levels of N-desethyloxybutynin appearing by the 2 hour sampling timepoint. Mean plasma N-desethyloxybutynin levels increased to a peak at 28 hours after dosing of 2.21 ng/mL, declined for approximately 12 hours before increasing to a $C_{max}$ of 2.72 ng/mL at 48 hours. The mean (SD) oxybutynin:N-desethyloxybutynin AUC ratio was 1:0.91.

Figure 13:
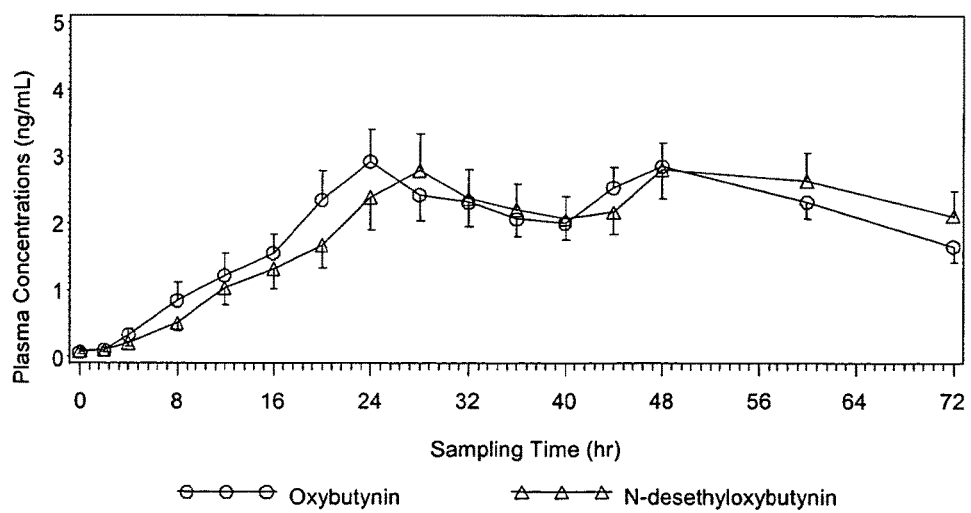
FIG. 13 is a graphical representation of the plasma concentrations of oxybutynin and N-desethyloxybutynin following topical application of 13.2% oxybutynin gel to a 400 cm² patch of skin area in accordance with the present invention.

FIG. 13 shows oxybutynin and N-desethyloxybutynin plasma concentrations following oxybutynin gel application to an 800 $cm^2$ application area for the duration of the study period. Plasma oxybutynin and N-desethyloxybutynin concentrations following gel application to an 800 $cm^2$ surface area produced similar kinetic profiles to the gel applications made to the 400 $cm^2$ area. Both oxybutynin and N-desethyloxybutynin levels were measurable by the 2 hour sample timepoint and gradually increased during the first 24 hours following dosing to peaks of 2.92 and 2.39 ng/mL for oxybutynin and N-desethyloxybutynin, respectively. Decreasing levels were observed for approximately the following 12 hours, followed by a rise to $C_{max}$ (3.80 and 3.40 ng/mL) at 48 hours for both oxybutynin and N-desethyloxybutynin.

Example 14: Topical Oxybutynin Chloride Gel

Example 14.1

TABLE 6

| Formulation[a] Et/W/G/D (% w/w) | $Q_t$ (t = 24 hours) (μg/cm$^2$/t)[b] | $J_{ss}$ (μg/cm$^2$/t)[b] |
|---|---|---|
| 74.5/20.0/1.5/4.0 | 11.37 ± 3.94 | 0.47 ± 0.16 |
| 69.5/25.0/1.5/4.0 | 10.99 ± 4.30 | 0.45 ± 0.14 |
| 64.5/30.0/1.5/4.0 | 10.02 ± 4.49 | 0.42 ± 0.19 |

[a]Et = ethanol; W = water; G = gelling agent = KLUCEL; D = drug = oxybutynin chloride
[b]Mean ± SD (n = 4 skin donors)

These results show that a formulation comprising about 65% to about 75% ethanol can be used effectively to delivery oxybutynin in a topical formulation.

Example 14.2

TABLE 7

| pH of gel | Formulation[a] Et/W/G/D/N (% w/w) | $Q_t$ (t = 24 hours) (μg/cm$^2$/t)[b] | $J_{ss}$ (μg/cm$^2$/t)[b] |
|---|---|---|---|
| 6.0 | 74.5/18.7/1.5/4.0/1.3 | 18.94 ± 5.12 | 0.79 ± 0.21 |
| 4.6 | 74.5/20.0/1.5/4.0/0 | 13.18 ± 4.96 | 0.55 ± 0.21 |

[a]Et = ethanol; W = water; G = gelling agent = klucel; D = drug = oxybutynin chloride (n = 4 skin donors) N = 2N NaOH
[b]Mean ± SD (n = 4 skin donors)

These results show that oxybutynin chloride gel with pH 6.0 produces higher oxybutynin skin permeation than that with pH 4.6. However, it is to be recognized that the formulation having a pH as low as about 4.6 provides a desirable flux rate, in certain aspects.

Example 14.3

TABLE 9

| Formulation[a] Et/W/Gl/G/D (% w/w) | $Q_t$ (t = 24 hours) (μg/cm$^2$/t)[b] | $J_{ss}$ (μg/cm$^2$/t)[b] |
|---|---|---|
| 73.2/20.4/0/2.0/4.4 | 10.66 ± 6.17 | 0.44 ± 0.26 |
| 73.2/19.4/1.0/2.0/4.4 | 10.86 ± 8.62 | 0.45 ± 0.36 |

[a]Et = ethanol; W = water; Gl = glycerin; G = gelling agent = klucel; D = drug = oxybutynin chloride
[b]Mean ± SD (n = 4 skin donors)

These results show that presence of glycerin in the oxybutynin chloride gel does not affect oxybutynin skin permeation through the skin. Therefore, glycerin can be included in an oxybutynin gel formulation as an emollient or other additive for reducing skin irritation or for other intended purposes that will be recognized by those skilled in the art.

Example 15: Topical Oxybutynin Chloride and Free Base Gel

TABLE 9

| Enhancer | Formulation[a] Et/W/E/G/D$_1$/D$_2$ (% w/w) | $Q_t$ (t = 24 hours) (μg/cm$^2$/t)[b] | $J_{ss}$ (μg/cm$^2$/t)[b] |
|---|---|---|---|
| None | 63.8/30.0/0/2.0/2.2/2.0 | 25.85 ± 15.35 | 1.08 ± 0.64 |
| Triacetin | 58.8/30.0/5.0/2.0/2.2/2.0 | 41.77 ± 27.99 | 1.74 ± 1.17 |

[a]Et = ethanol; E = enhancer; W = water; G = gelling agent = KLUCEL; D$_1$ = drug = oxybutynin chloride; D$_2$ = drug = oxybutynin free base
[b]Mean ± SD (n = 4 skin donors)

These results show that triacetin significantly increases the skin flux of total oxybutynin as compared to the gel formulation without triacetin.

Example 16: Topical Oxybutynin Chloride Gel and Flux Over Time Data

A free form oxybutynin chloride gel was prepared having a composition of 73.3 wt % ethanol, 18.0 wt % water, 1.0 wt % glycerin, 2.0 wt % KLUCEL HF, 4.4 wt % oxybutynin chloride, and 1.3 wt % sodium hydroxide. The resulting gel had a pH of 6. Nine separate skin samples were tested for flux over a period of 48 hours and the results are shown in Table 10. After 24 hours of sampling, the remaining gel on the top of the skin was removed and then the 30 hour samples (6 hours after gel removal) and 48 hour samples (24 hours after gel removal) were taken.

TABLE 10

| | Mean Cumulative Permeation Time | | | |
|---|---|---|---|---|
| Sample | 6 hr | 24 hr | 30 hr | 48 hr |
| 1 | 1.42 ± 2.01 | 4.57 ± 1.53 | 8.20 ± 0.40 | 11.95 ± 2.14 |
| 2 | 9.41 ± 0.58 | 19.61 ± 6.71 | 31.82 ± 7.37 | 46.43 ± 8.72 |
| 3 | 4.59 ± 2.68 | 14.12 ± 7.17 | 16.15 ± 9.81 | 24.77 ± 11.83 |
| 4 | 3.90 ± 1.23 | 9.40 ± 4.27 | 14.84 ± 6.70 | 26.47 ± 14.34 |
| 5 | 3.99 ± 3.28 | 16.17 ± 6.05 | 26.43 ± 7.89 | 38.35 ± 9.74 |
| 6 | 1.44 ± 0.43 | 3.70 ± 0.67 | 5.66 ± 1.06 | 8.75 ± 1.60 |
| 7 | 3.03 ± 0.45 | 7.39 ± 1.89 | 10.03 ± 2.66 | 15.17 ± 4.25 |
| 8 | 6.62 ± 1.51 | 17.23 ± 3.24 | 27.27 ± 8.93 | 42.98 ± 18.02 |
| 9 | 4.20 ± 0.95 | 13.73 ± 3.06 | 20.49 ± 4.52 | 32.19 ± 5.50 |
| Mean | 4.29 ± 2.50 | 11.77 ± 5.72 | 17.84 ± 9.20 | 27.45 ± 13.65 |

In one aspect, an oxybutynin gel formulation for topical application is provided that delivers oxybutynin at a mean flux rate of from about 1.5 to about 7.0 ug/cm2/hr at about 6 hrs after application. In another aspect, an oxybutynin gel formulation for topical application is provided that delivers oxybutynin at a mean flux rate of from about 6 to about 17 ug/cm2/hr at about 24 hrs after application. In yet another aspect, an oxybutynin gel formulation for topical application is provided that delivers oxybutynin at a mean flux rate of from about 8 to about 27 ug/cm2/hr at about 30 hrs after application. In yet another aspect, an oxybutynin gel formulation for topical application is provided that delivers oxybutynin at a mean flux rate of from about 14 to about 40 ug/cm2/hr at about 48 hrs after application. In another aspect, an oxybutynin gel formulation for topical application is provided that delivers oxybutynin at a mean flux rate of from about 1.5 to about 7.0 ug/cm2/hr at about 6 hrs after application; from about 6 to about 17 ug/cm2/hr at about 24 hrs after application; from about 8 to about 27 ug/cm2/hr at about 30 hrs after application; and from about 14 to about 40 ug/cm2/hr at about 48 hrs after application. The oxybutynin can be present as a free base or as a pharmaceutically acceptable salt (e.g., such as HCl) or a mixture thereof. In yet another aspect, the oxybutynin can be present as its R-isomer or S-isomer, or their pharmaceutically acceptable salts or mixtures thereof. When the oxybutynin is present as its corresponding isomer, in some aspects, the mean flux rates for that isomer may be as following: from about 0.7 to about 5.0 ug/cm2/hr at about 6 hrs after application; from about 3 to about 9 ug/cm2/hr at about 24 hrs after application; from about 4 to about 14 ug/cm2/hr at about 30 hrs after application; from about 6 to about 25 ug/cm2/hr at about 48 hrs after application.

The above flux rates deliver therapeutic levels of oxybutynin to a subject in need thereof. Such therapeutic plasma levels may range from about 1.4 ng/ml to about 8 ng/ml, and in certain aspects, the plasma concentration may range from about 1.42 ng/ml to about 4 ng/ml. In another aspect, the plasma concentration may range from about 1.8 ng/ml to about 4 ng/ml. In yet another aspect, the plasma concentration may range from about 1.8 ng/ml to about 3 ng/ml.

Example 17: Topical Oxybutynin Cream

A free form oxybutynin cream containing the compositions in each phase as shown in Table 11 may be produced. Oxybutynin is present in the formulation at from about 1 to about 10% w/w.

TABLE 11

| Phase | Component | % w/w |
|---|---|---|
| Water | Water | 20-60 |
|  | Propylene Glycol | 1-10 |
|  | Sodium Stearoyl Lactate | 0-5 |
|  | 20% PLURONIC 270 | 0-50 |
|  | Methyl Paraben | 0-0.5 |
| Oil | Oleic Acid | 0-20 |
|  | Cetyl Alcohol | 0-20 |
|  | Glycerol Monooleate | 0-10 |
|  | Lauryl Acetate | 0-10 |
|  | Propyl Paraben | 0-0.5 |

Example 18: Topical Oxybutynin Lotion

A free form oxybutynin lotion containing the compositions in each phase as shown in Table 12 may be produced. Oxybutynin is present in the formulation at from about 1 to about 10% w/w.

TABLE 12

| Phase | Component | % w/w |
|---|---|---|
| Water | Water | 20-90 |
|  | Distearyl Dimonium Chloride | 1-5 |
|  | Sodium Chloride | 0-5 |
|  | Methyl Paraben | 0-0.5 |
| Oil | Glycerin | 0-20 |
|  | Petrolatum | 0-10 |
|  | Isopropyl Palmitate | 0-5 |
|  | Cetyl Alcohol | 0-10 |
|  | Dimethicone | 0-5 |
|  | Propyl Paraben | 0.0.5 |

Example 19: Topical Oxybutynin Emulsified Gel

A free form oxybutynin gel containing the compositions in each phase as shown in Table 13 may be produced. Oxybutynin is present in the formulation at from about 1 to about 10% w/w. A free form oxybutynin gel may be produced using an emulsified gel carrier. Oxybutynin is present in the formulation from about 1 to about 20% w/w. Based on the forgoing, it is expected that the pH effects shown in the other applicable examples can be observed in certain aspects of these formulations. Further, the emulsified gel bases are expected to deliver oxybutynin either in its free base form, in the form of a pharmaceutically acceptable salt, or in a mixture thereof, analogous to the above-recited examples, with delivery rates equivalent thereto. In addition, it is to be understood that oxybutynin can be present in its R- or S-isomeric forms.

TABLE 13

| Phase | Component | % w/w |
|---|---|---|
| Water | Water | 30-90 |
|  | Propylene Glycol | 1-10 |
| Oil | Sodium Stearoyl Lactate | 0-5 |
|  | 20% PLURONIC 270 | 0-20 |
|  | Silicone Dioxide | 0-1 |
|  | Methyl Paraben | 0-0.5 |
|  | CARBOPOL | 0.1-5 |
|  | Oleic Acid | 0-10 |
|  | Cetyl Alcohol | 0-10 |
|  | Glycerol Monooleate | 0-10 |
|  | Lauryl Acetate | 0-10 |
|  | Propyl Paraben | 0-0.5 |

Example 20: Topical Oxybutynin Ointment

A free form oxybutynin ointment containing the compositions in each phase as shown in Table 14 may be produced.

TABLE 14

| Component | % w/w |
|---|---|
| Cholesterol | 0-5 |
| Stearyl Alcohol | 0-5 |
| White Wax | 0-10 |
| White Petrolatum | 70-100 |
| Oxybutynin | 1-10 |

Example 21: Oxybutynin Free Form Gel Containing Optical Isomers

Table 15 shows the skin flux measured over a 24 hour period for each of the R and S isomers in the chloride and free base forms. Both oxybutynin free base and oxybutynin chloride are chiral molecules that exists in two forms, R and S and were each tested in their optically pure forms according to the present invention as shown in Table 15.

TABLE 15

|  | Formulation[a] Et/W/Gl/G/$D_1$/N (% w/w) 73.2/17.9/1.0/2.0/4.4/1.5 | Formulation[a] Et/W/Gl/G/$D_2$/H (% w/w) 73.2/18.3/1.0/2.0/4.0/1.5 |
|---|---|---|
|  | $Q_t$ (t = 24 hours) ($\mu g/cm^2/t$)[b] | |
| R-Oxybutynin | 6.98 ± 4.26 | 7.08 ± 5.43 |
| S-Oxybutynin | 6.24 ± 3.77 | 6.87 ± 5.35 |

[a]Et = ethanol; W = water; G = gelling agent = KLUCEL; Gl = glycerin $D_1$ = oxybutynin chloride; $D_2$ = oxybutynin free base N = 2N sodium hydroxide (NaOH); H = 2H Hydrochloride (HCl)

TABLE 15-continued

| Formulation$^a$ Et/W/Gl/G/D$_1$/N (% w/w) 73.2/17.9/1.0/2.0/4.4/1.5 | Formulation$^a$ Et/W/Gl/G/D$_2$/H (% w/w) 73.2/18.3/1.0/2.0/4.0/1.5 |
|---|---|
| $Q_t$ (t = 24 hours) ($\mu g/cm^2/t$)$^b$ | |

$^b$Mean ± SD (n = 3 skin donors)

These results show that the R and S isomers from both oxybutynin free base gel and oxybutynin chloride gel permeate through the skin in equal amounts. Further, these results show that oxybutynin chloride can be delivered at about the same rate as oxybutynin free base from a topically applied unoccluded gel.

It is to be understood that the above-described compositions and modes of application are only illustrative of preferred embodiments of the present invention. Numerous modifications and alternative arrangements may be devised by those skilled in the art without departing from the spirit and scope of the present invention and the appended claims are intended to cover such modifications and arrangements.

Thus, while the present invention has been described above with particularity and detail in connection with what is presently deemed to be the most practical and preferred embodiments of the invention, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. A method of treating a human patient with an over active bladder comprising the step of applying about 1 to about 3 grams of an unoccluded oxybutynin gel formulation once a day to 133 cm² to 800 cm² of the outer skin surface of the human patient's chest, abdomen, upper arms and/or thighs, wherein, the unoccluded oxybutynin gel formulation comprises:
   (i) about 4 wt % to about 13.2 wt % of oxybutynin wherein the oxybutynin is oxybutynin free base, oxybutynin chloride or a mixture of oxybutynin free base and oxybutynin chloride;
   (ii) about 1 wt % to about 30 wt % water;
   (iii) about 0.1 wt % to about 5 wt % of a gelling agent;
   (iv) about 65 wt % to about 80 wt % of a solvent selected from the group consisting of ethanol, isopropanol, propanol, methanol, and mixtures thereof;
wherein the unoccluded oxybutynin gel formulation has a pH of about 6.0 to about 10.0 and wherein a single dose application of the unoccluded oxybutynin gel to 133 cm' to 800 cm² of the outer skin surface of the human patient's chest, abdomen, upper arms and/or thighs produces an increasing mean plasma oxybutynin level for 24 hours following application of the unoccluded gel, a mean plasma area under the curve (AUC) ratio of oxybutynin to N-desethyloxybutynin of from about 0.8:1 to about 2.5:1; a mean N-desethyloxybutynin plasma level of from about 0.5 ng/ml to about 5 ng/ml; and a mean (R)—N-desethyloxybutynin plasma level of from about 0.25 ng/ml to about 4 ng/ml and wherein oxybutynin is the only drug in the unoccluded oxybutynin gel formulation.

2. The method of claim 1 wherein the unoccluded oxybutynin gel formulation further comprises additional components selected from the group consisting of emulsifiers, chelating agents, surfactants, emollients, preservatives, antioxidants, lubricants, pH adjusters, dyes, and perfumes.

3. The method of claim 1 wherein the gelling agent for the unoccluded oxybutynin gel is selected from the group consisting of hydroxypropyl cellulose, hydroxypropylmethyl cellulose, or hydroxyethyl cellulose.

4. A method of treating a human patient with an over active bladder comprising the step of applying about 1 to about 3 grams of an unoccluded oxybutynin gel formulation once a day to 133 cm² to 800 cm² of the outer skin surface of the human patient's chest, abdomen, upper arms and/or thighs, wherein the unoccluded oxybutynin gel formulation consists of:
   (i) about 4 wt % to about 13.2 wt % of oxybutynin chloride;
   (ii) about 1 wt % to about 30 wt % water;
   (iii) about 0.1 wt % to about 5 wt % of a gelling agent selected from the group consisting of hydroxypropyl cellulose, hydroxypropylmethyl cellulose, or hydroxyethyl cellulose;
   (iv) about 65 wt % to about 80 wt % of a solvent selected from the group consisting of ethanol, isopropanol, propanol, methanol, and mixtures thereof;
   (v) up to about 10% of glycerin;
   (vi) optionally a pH additive; and
   (vii) optionally additional components selected from the group consisting of preservatives, antioxidants, dyes, and perfumes;
wherein the unoccluded oxybutynin gel formulation has a pH of about 6.0 to about 10.0 and wherein a single dose application of the unoccluded oxybutynin gel to 133 cm² to 800 cm² of the outer skin surface of the human patient's chest, abdomen, upper arms and/or thighs produces an increasing mean plasma oxybutynin level for 24 hours following application of the unoccluded gel, a mean plasma area under the curve (AUC) ratio of oxybutynin to N-desethyloxybutynin of from about 0.8:1 to about 2.5:1; a mean N-desethyloxybutynin plasma level of from about 0.5 ng/ml to about 5 ng/ml; and a mean (R)—N-desethyloxybutynin plasma level of from about 0.25 ng/ml to about 4 ng/ml and wherein oxybutynin is the only drug in the unoccluded oxybutynin gel formulation.

5. The method of claim 1, wherein the unoccluded oxybutynin gel formulation is applied once a day to 200 cm² to 800 cm² of the outer skin surface of the human patient's chest, abdomen, upper arms and/or thighs.

6. The method of claim 4, wherein the unoccluded oxybutynin gel formulation is applied once a day to 200 cm² to 800 cm² of the outer skin surface of the human patient's chest, abdomen, upper arms and/or thighs.

7. The method of claim 1, wherein the unoccluded oxybutynin gel formulation is applied once a day to 400 cm² to 800 cm² of the outer skin surface of the human patient's chest, abdomen, upper arms and/or thighs.

8. The method of claim 4, wherein the unoccluded oxybutynin gel formulation is applied once a day to 400 cm² to 800 cm² of the outer skin surface of the human patient's chest, abdomen, upper arms and/or thighs.

* * * * *